(12) United States Patent
Okitsu et al.

(10) Patent No.: US 7,130,245 B2
(45) Date of Patent: Oct. 31, 2006

(54) ULTRASONIC DOUBLE FEED DETECTING DEVICE

(75) Inventors: Katsuhiko Okitsu, Saitama (JP); Tomoya Shimazaki, Gunma (JP)

(73) Assignee: Canon Denshi Kabushiki Kaisha (JP)

( * ) Notice: Subject to any disclaimer, the term of this patent is extended or adjusted under 35 U.S.C. 154(b) by 313 days.

(21) Appl. No.: 10/763,513

(22) Filed: Jan. 23, 2004

(65) Prior Publication Data

US 2004/0150155 A1    Aug. 5, 2004

(30) Foreign Application Priority Data

Jan. 31, 2003  (JP)  .............................. 2003-025014
Jan. 31, 2003  (JP)  .............................. 2003-025015

(51) Int. Cl.
  *G01S 3/80*   (2006.01)
  *B65H 7/12*   (2006.01)

(52) U.S. Cl. ..................... 367/125; 367/124; 271/262; 271/265.04

(58) Field of Classification Search ............... 271/262, 271/263, 265.04, 259, 265.01, 258.01, 265.02; 367/124, 93, 125
See application file for complete search history.

(56) References Cited

U.S. PATENT DOCUMENTS

| 4,066,969 A * | 1/1978 | Pearce et al. ............ 367/125 |
| 4,368,438 A * | 1/1983 | Stienstra ................... 73/159 |
| 6,397,671 B1 * | 6/2002 | Nishio et al. .............. 271/263 |
| 6,511,064 B1 * | 1/2003 | Phinney et al. ............ 271/262 |
| 6,520,498 B1 * | 2/2003 | Phinney ..................... 271/263 |
| 6,739,591 B1 * | 5/2004 | Chujo et al. .............. 271/262 |
| 2002/0079644 A1 | 6/2002 | Phinney |

FOREIGN PATENT DOCUMENTS

| DE | 36 20 042 A1 | 1/1987 |
| EP | 0 033 552 A1 | 8/1981 |
| EP | 1 148 012 A2 | 10/2001 |
| JP | 57 170347 A | 10/1982 |
| JP | 5-40030 | 2/1993 |
| JP | 05 040030 A | 2/1993 |
| JP | 2000-211769 | 8/2000 |
| JP | 2000-211769 A | 8/2000 |

OTHER PUBLICATIONS

Relevant portion of Search Report issued on Aug. 5, 2005 for counterpart application EP 04 00 2088.

* cited by examiner

*Primary Examiner*—Ian J. Lobo
(74) *Attorney, Agent, or Firm*—Kimms & McDowell LLP

(57) ABSTRACT

A double feed detecting apparatus provided with an ultrasonic transmitter installed on one side of a transport path for a sheet material for transmitting an ultrasonic toward the sheet material, an ultrasonic receiver installed on the other side of the transport path for the sheet material for receiving the ultrasonic transmitted by the ultrasonic transmitter and outputting a received ultrasonic signal, a first determining device for determining whether double feed or not in accordance with the amplitude of the received ultrasonic signal output by the ultrasonic receiver, and a second determining device for detecting a phase change in the received ultrasonic signal, and determining whether double feed or not on the basis of the detected phase change.

19 Claims, 21 Drawing Sheets

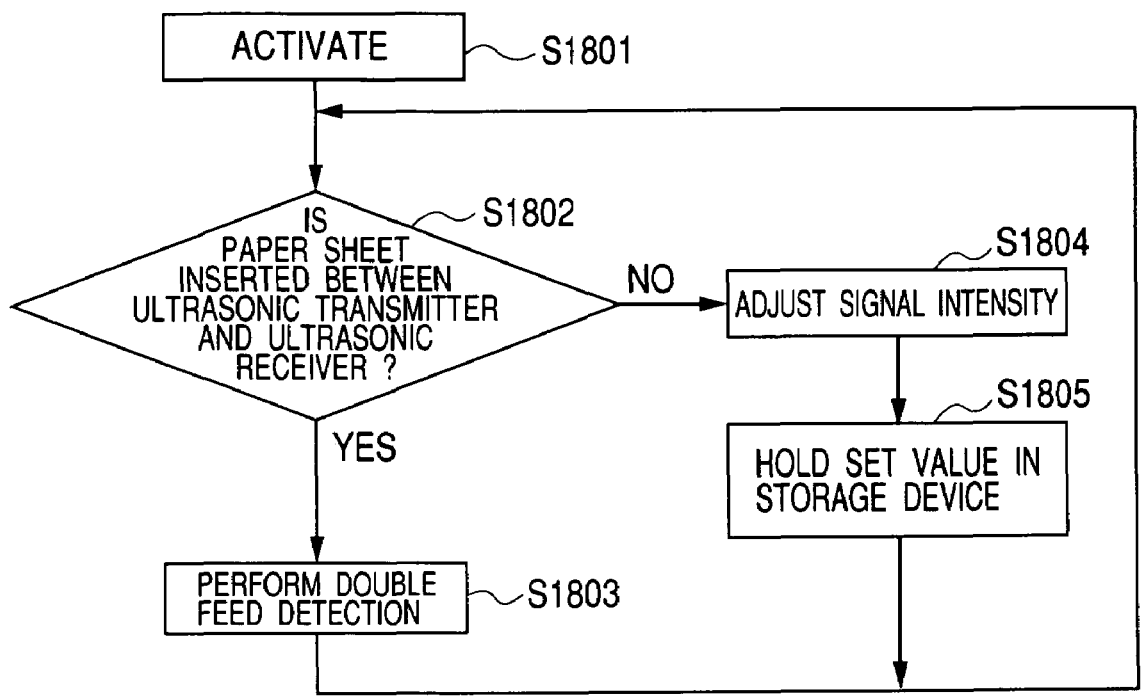

ULTRASONIC DOUBLE FEED DETECTING DEVICE

BACKGROUND OF THE INVENTION

1. Field of the Invention

The invention relates to a double feed detecting apparatus for detecting double feed which is a phenomenon of transporting two or more sheet materials as they are lying one upon another, particularly by the utilization of an ultrasonic sensor, in an apparatus carrying a plurality of sheet materials thereon and having the function of separating and transporting the sheet materials one by one.

2. Related Background Art

In a scanner, a printer, a copying machine, a printer, an automated teller machine (ATM) or the like, there is provided a mechanism for separating and transporting sheet materials one by one. However, there is conceived the possibility that when only one sheet material should be transported, double feed which is a phenomenon of two or more sheet materials being transported while they partly or entirely overlapping one another occurs. Therefore, in an apparatus for transporting sheet materials, the function of detecting the double feed of the sheet materials becomes necessary. As a mechanism for detecting the double feed of sheet materials, a double feed detecting apparatus utilizing an ultrasonic is popular in each field. With bank notes (paper money) as an example of the sheet materials, description will hereinafter be made of a double feed detecting apparatus for detecting the double feed of the bank notes.

FIG. 20 of the accompanying drawings shows the epitome of a conventional bank note double feed detecting apparatus. In FIG. 20, the reference numeral 101 designates sheet materials to be detected, which herein are shown as bank notes. The reference numeral 102 denotes an ultrasonic transmitter which transmits an ultrasonic for the bank notes 101. The reference numeral 103 designates an ultrasonic receiver which receives the ultrasonic transmitted by the ultrasonic transmitter 102. Also, as shown in FIG. 20, the ultrasonic receiver 103 is installed so as to be opposed to the ultrasonic transmitter 102 with the transport path of the bank notes 101 interposed therebetween so as to be capable of receiving the ultrasonic transmitted through the bank notes 101. The reference numeral 108 denotes a wave analyzer which analyzes the reception signal of the ultrasonic received by the ultrasonic receiver 103.

Description will now be made of the operation of the double feed detecting apparatus shown in FIG. 20.

First, the ultrasonic transmitted from the ultrasonic transmitter 102 impinges on the bank notes 101, and the transmitted wave thereof is received by the ultrasonic receiver 103. Thereby, the ultrasonic receiver 103 outputs an output voltage varied in accordance with the reception intensity of the received ultrasonic. The wave analyzer 108 analyzes a variation in the output voltage output by the ultrasonic receiver 103 as an ultrasonic reception signal.

The double feed detecting technique of FIG. 20 is what is called a level determining process of detecting double feed by the wave analyzer 108 analyzing any change in the amplitude of the received ultrasonic. A double feed detecting method using this level determining process is described, for example, in Japanese Patent Application Laid-Open No. H5-40030.

The level determining process will be further described hereinafter. First, a double feed determining threshold value is set in advance, whereafter the bank notes 101 are transported and the ultrasonic receiver 103 obtains the amplitude of the ultrasonic transmitted through the bank notes 101. As compared with the amplitude of the transmitted ultrasonic when the bank notes 101 are properly transported one by one, the amplitude of the transmitted ultrasonic when the bank notes 101 are double-fed assumes a small value because the amount of attenuation of the ultrasonic becomes great. Accordingly, the amplitude of the ultrasonic obtained by the ultrasonic receiver 103 is compared with the aforementioned double feed determining threshold value in the wave analyzer 108, whereby it is possible to detect the double feed of the bank notes 101 from the result of the comparison.

In the level determining process according to the prior art, however, when the sheet materials transported are very thin, the amount of attenuation of the ultrasonic is small even if the sheet materials are double-fed, and as compared with a case where the sheet materials are properly transported, a great difference does not appear in the reception intensity of the ultrasonic and therefore, the determination of double feed detection becomes difficult.

Also, as another double feed detecting technique, there is a technique called a phase determining process of detecting the double feed of sheet materials by a phase variation in the waveform of a received ultrasonic. A double feed detecting method using this phase determining process is described, for example, in Japanese Patent Application Laid-Open No. 2000-211769.

To effect the detection of the double feed of sheet materials by this phase determining process, it is necessary to construct a complicated analog signal comparison circuit, and sampling data corresponding to a wavelength of a received signal waveform is obtained and at the same time, it is held in a storage device and the received signal is analyzed and therefore, a great burden is applied to a control circuit, and this leads to the problem that an integrated circuit (IC) for exclusive use and a control circuit having a high function become necessary.

Further, the above-described phase determining process suffers from the problem that the received ultrasonic signal is affected by changes in external factors such as the distance between sensors, the thickness of the sheet material, ambient temperature and humidity and the atmospheric pressure, and the accuracy of double feed detection is reduced. The phase determining process also suffers from the problem that when the sheet materials of which the double feed is to be detected are thick, the amplitude of the ultrasonic signal is greatly attenuated in case of double feed and the ultrasonic signal is hardly distinguishable from the noise signal of the ultrasonic receiver itself or an external device and thus, a waveform sufficient to enable the phase thereof to be determined may not be output.

FIG. 21 of the accompanying drawings shows another example of the conventional double feed detecting apparatus. In FIG. 21, the reference numeral 101 designates sheet materials to be detected, which herein are shown as bank notes. The reference numeral 102 denotes an ultrasonic transmitter which transmits an ultrasonic to the bank notes 101. The reference numeral 103 designates an ultrasonic receiver which receives the ultrasonic transmitted by the ultrasonic transmitter 102. Also, as shown in FIG. 21, the ultrasonic receiver 103 is installed so as to be opposed to the ultrasonic transmitter 102 with the transport path of the bank notes 101 interposed therebetween so as to be capable of receiving the ultrasonic transmitted through the bank notes 101.

The reference numeral 104 denotes a control circuit which supplies a pulse signal of 200 kHz as a transmitted ultrasonic signal to a drive circuit 105. The drive circuit 105 amplifies the pulse signal supplied from the control circuit 104 and outputs an ultrasonic pulse signal. Thereby, the ultrasonic transmitter 102 transmits an ultrasonic of 200 kHz on the basis of the amplified ultrasonic pulse signal. The transmitted ultrasonic signal supplied by the control circuit 104 is, for example, a signal which transmits a pulse signal of 200 kHz over a constant time for several periods. This is what is generally called a burst-wave, and the burst-wave is periodically transmitted once in several milliseconds (ms).

The reference numeral 106 designates an amplifier circuit which amplifies the received ultrasonic signal output by the ultrasonic receiver 103. This is because when the bank notes 101 which are to be transported come into between the ultrasonic transmitter 102 and the ultrasonic receiver 103, the ultrasonic signal transmitted from the ultrasonic transmitter 102 is attenuated, and becomes a very feeble signal before it reaches the ultrasonic receiver 103 and therefore, the received ultrasonic signal output by the ultrasonic receiver 103 becomes feeble in amplitude, and this signal must be amplified by the amplifier circuit 106 and be raised to a signal amplitude capable of effecting double feed detection judgment. The reference numeral 110 denotes a signal gain adjusting circuit 110 which adjusts the signal gain of the amplifier circuit 106. Here, the signal gain adjusting circuit 110 is e.g., a volume. Also, the adjustment of this signal gain is effected for individual products, for example, before the shipment of the products, or is effected by the user of the products.

The reference numeral 107 designates an A-D converter which converts the received ultrasonic signal (analog signal) amplified by the amplifier circuit 106 into a digital signal and outputs it to a signal analyzing circuit 108. The signal analyzing circuit 108 analyzes the received ultrasonic signal digitized in the A-D converter 107, and outputs the result of the analysis to the control circuit 104. The reference numeral 109 denotes a storage device which holds therein each set value of the double feed detecting apparatus shown in FIG. 21. Thereby, the double feed detecting apparatus shown in FIG. 21 performs a double feed detecting operation by the use of the set values held in the storage device 109.

Description will now be made of the operation of the double feed detecting apparatus shown in FIG. 21.

First, the ultrasonic transmitted from the ultrasonic transmitter 102 impinges on the bank note 101, and the transmitted wave thereof is received by the ultrasonic receiver 103. Thereby, the ultrasonic receiver 103 outputs a received ultrasonic signal varied in accordance with the reception intensity of the received ultrasonic. Next, the amplifier circuit 106 amplifies the received ultrasonic signal output by the ultrasonic receiver 103 at an amplification factor conforming to the adjustment by the signal gain adjusting circuit 110. Next, the A-D converter 107 converts the received ultrasonic signal amplified by the amplifier circuit 106 into a digital signal, and outputs the digitized received ultrasonic signal to the signal analyzing circuit 108. Next, the signal analyzing circuit 108 analyzes the digitized received ultrasonic signal output by the A-D converter 107. Next, the control circuit 104, when it judges double feed on the basis of the result of the analysis by the signal analyzing circuit 108, performs the process of informing the apparatus or the utilizer of the apparatus to the effect that double feed has occurred.

The double feed detecting method of FIG. 21 is the aforedescribed level determining process of analyzing a variation in the amplitude of the received ultrasonic signal by the signal analyzing circuit 108 to thereby detect double feed. This level determining process will be further described below. First, a double feed determining threshold value is set in advance, whereafter, the bank note 101 is transported and the ultrasonic receiver 102 obtains the amplitude of an ultrasonic transmitted through the bank note 101. As compared with the amplitude of the transmitted ultrasonic when the bank notes 101 are properly transported one by one, the amplitude of the transmitted ultrasonic when the bank notes 101 are double-fed assumes a small value because the amount of attenuation of the ultrasonic becomes great. Accordingly, the amplitude of the received ultrasonic signal obtained by the ultrasonic receiver 102 and amplified by the amplifier circuit 106 is compared with the aforementioned double feed determining threshold value in the wave analyzing circuit 108, whereby it is possible to detect the double feed of the bank notes 101.

As a problem in the conventional double feed detecting apparatus, there is the problem that differences in signal amplification factor and resonance frequency occur to each product due to the unevenness of the characteristics of the ultrasonic transmitter 102 and the ultrasonic receiver 103 and the unevenness of the constituent parts of the amplifier circuit 106 and therefore, it is necessary to adjust the signal amplification factors of individual products before the shipment of the products, and this leads to an increase in cost.

Also, there is the problem that even if as described above, the signal amplification factors of the individual products are adjusted before the shipment of the products, the signal intensity of the received ultrasonic signal is varied by changes in external factors such as the distance between the ultrasonic transmitter 102 and the ultrasonic receiver 103, the ambient temperature and humidity and the atmospheric pressure, and the accuracy of double feed detection is reduced.

Further, there is the problem that the burst transmission interval of an ultrasonic generating signal is always effected at a constant period and therefore, when an interceptor is inserted between the ultrasonic transmitter 102 and the ultrasonic receiver 103, whereby the reverberation of the ultrasonic is quickly attenuated, the transmission of the next burst-wave is waited for for an excess time, and this leads to the bad efficiency of burst transmission.

SUMMARY OF THE INVENTION

The present invention has been made in view of the above-noted circumstances and an object thereof is to provide a double feed detecting apparatus which reliably realizes the detection of the double feed of sheet materials irrespective of changes in external factors such as the distance between sensors, the thickness of the sheet materials, the ambient temperature and humidity, and the atmospheric pressure.

Also, an object of the present invention is to provide a double feed detecting apparatus which does not effect the change of the construction of an amplifier circuit or the adjustment of an amplification factor, but can control a transmitting method and a receiving method for an ultrasonic to thereby properly adjust the signal intensity of a received ultrasonic signal.

Also, an object of the present invention is to provide a double feed detecting apparatus which varies the burst transmission interval of an ultrasonic generating signal to thereby suitably change the number of times over which a received ultrasonic signal can be sampled per unit time and increase the sampling number, whereby the accuracy of double feed detection can be improved.

In order to achieve the above objects, the double feed detecting apparatus of the present invention has ultrasonic transmitting means installed on one side of a transport path for a sheet material for transmitting an ultrasonic toward the sheet material, ultrasonic receiving means installed on the other side of the transport path for the sheet material for receiving the ultrasonic transmitted by the ultrasonic transmitting means and outputting a received ultrasonic signal, first double feed determining means for determining whether double feed or not in accordance with the amplitude of the received ultrasonic signal output by the ultrasonic receiving means, and second double feed determining means for detecting a change in the phase of the received ultrasonic signal, and determining whether double feed or not on the basis of the detected change in the phase.

Also, the double feed detecting apparatus of the present invention has ultrasonic transmitting means installed on one side of a transport path for a sheet material for transmitting an ultrasonic toward the sheet material, ultrasonic receiving means installed on the other side of the transport path for the sheet material for receiving the ultrasonic transmitted by the ultrasonic transmitting means and outputting a received ultrasonic signal, control means for controlling the obtaining timing of the received ultrasonic signal and/or the characteristic of the ultrasonic transmitted by the ultrasonic transmitting means to adjust the amplitude of the received ultrasonic signal output by the ultrasonic receiving means, and signal analyzing means for analyzing whether double feed or not on the basis of a change in the amplitude of the received ultrasonic signal output by the ultrasonic receiving means adjusted by the control means.

Also, the double feed detecting apparatus of the present invention has ultrasonic transmitting means installed on one side of a transport path for a sheet material for transmitting an ultrasonic of a burst-wave toward the sheet material at any time interval, ultrasonic receiving means installed on the other side of the transport path for the sheet material for receiving the ultrasonic transmitted by the ultrasonic transmitting means and outputting a received ultrasonic signal, signal analyzing means for analyzing whether or not double feed on the basis of a change in the amplitude of the received ultrasonic signal output by the ultrasonic receiving means, and a change in a convergence time required for the received ultrasonic wave to converge, and control means for controlling the ultrasonic transmitting means so as to change the time interval at which the ultrasonic is transmitted in accordance with the convergence time analyzed by the signal analyzing means.

Other objects and features of the present invention will become apparent from the following description and the accompanying drawings.

BRIEF DESCRIPTION OF THE DRAWINGS

FIG. 17 is a flow chart showing the operation of the double feed detecting apparatus 10.

DESCRIPTION OF THE PREFERRED EMBODIMENTS

Some embodiments of the present invention will hereinafter be described with reference to the drawings.

Description will first be made of the schematic construction of a double feed detecting apparatus which is an embodiment of the present invention.

Figure 1:
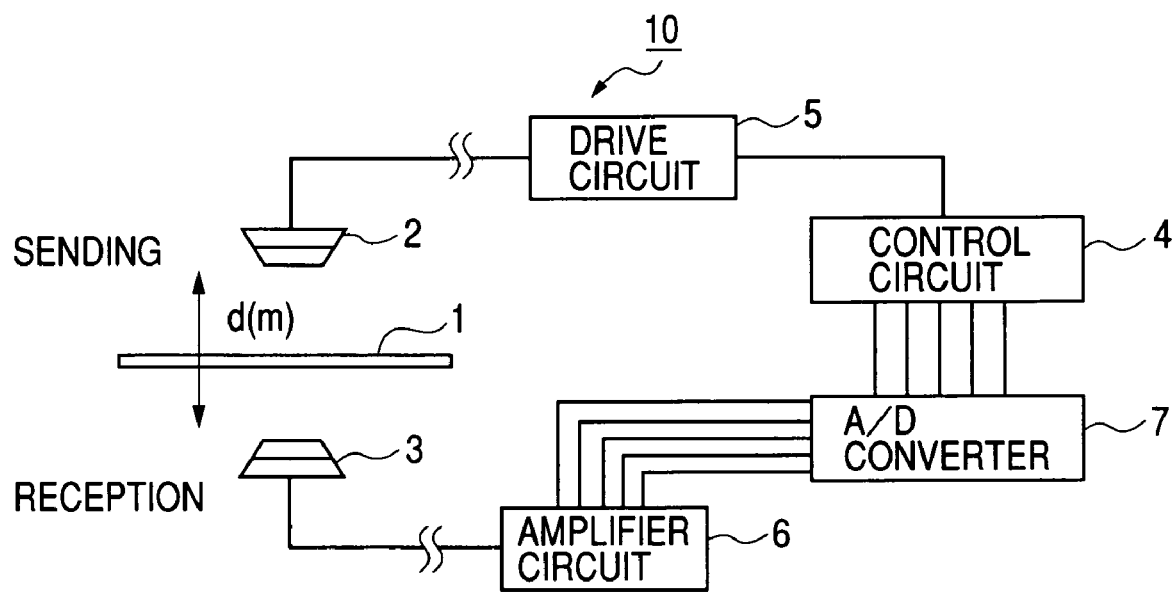
FIG. 1 schematically shows the construction of a double feed detecting apparatus according to an embodiment of the present invention.

FIG. 1 schematically shows the construction of the double feed detecting apparatus according to an embodiment of the present invention. The double feed detecting apparatus 10 shown in FIG. 1 is an apparatus utilizing an ultrasonic sensor to detect double feed in which two or more sheets of paper (sheet materials) are transported. The reference numeral designates paper which is a sheet material to be transported. That is, the double feed detecting apparatus 10 detects the double feed of the paper 1. While in the present embodiment, description is made with paper taken as an example of the sheet material, this is not restrictive, but the sheet material may be film or a bank note or the like.

The reference numeral 2 denotes an ultrasonic transmitter which transmits an ultrasonic to the paper 1. Specifically, the ultrasonic transmitter 2 transmits an ultrasonic signal when an ultrasonic pulse signal from a drive circuit 5 which will be described later is input thereto. The reference numeral 3 designates an ultrasonic receiver which receives the ultrasonic transmitted by the ultrasonic transmitter 2. As shown in FIG. 1, the ultrasonic receiver 3 is installed so as to be opposed to the ultrasonic transmitter 2 with a transport path for the paper 1 interposed therebetween so as to be capable of receiving the ultrasonic transmitted through the paper 1. Thereby, the ultrasonic transmitted from the ultrasonic transmitter 2 impinges on the paper 1, and the ultrasonic receiver 3 receives the transmitted wave. Also, the ultrasonic receiver 3 outputs an output voltage varying in accordance with the reception intensity of the received ultrasonic.

As described above, when the paper 1 exists on the transport path, the ultrasonic transmitted through the paper 1 is received by the ultrasonic receiver 3, but when the paper 1 does not exist on the transport path, the ultrasonic transmitted by the ultrasonic transmitter 2 is intactly received by the ultrasonic receiver 3.

The reference numeral 4 denotes a control circuit which supplies a pulse signal of 200 kHz as a transmitted ultrasonic signal to a drive circuit 5. The drive circuit 5 amplifies the pulse signal supplied from the control circuit 4 and outputs an ultrasonic pulse signal. Thereby, the ultrasonic transmitter 2 transmits an ultrasonic of 200 kHz on the basis of the signal-amplified ultrasonic pulse signal. The transmitted ultrasonic signal supplied by the control circuit 4 is, for example, a signal transmitting a pulse signal of 200 kHz corresponding to several periods extending for a constant time. This is what is generally called a burst-wave, which is periodically transmitted once in several milliseconds (ms).

The reference numeral 6 designates an amplifier circuit which amplifies the output signal output by the ultrasonic receiver 3. This is because when the paper 1 to be transported comes into between the ultrasonic transmitter 2 and the ultrasonic receiver 3, the ultrasonic signal transmitted from the ultrasonic transmitter 2 is attenuated and becomes a very feeble signal before it reaches the ultrasonic receiver 3 and therefore, the output signal of the ultrasonic receiver 3 also becomes feeble in amplitude, and this must be amplified by the amplifier circuit 6 and be raised to a signal amplitude capable of detecting and judging double feed. The reference numeral 7 denotes an A-D converter which converts the received ultrasonic signal (analog signal) amplified by the amplifier circuit 6 into a digital signal and outputs it to the control circuit 4.

Figure 2A:
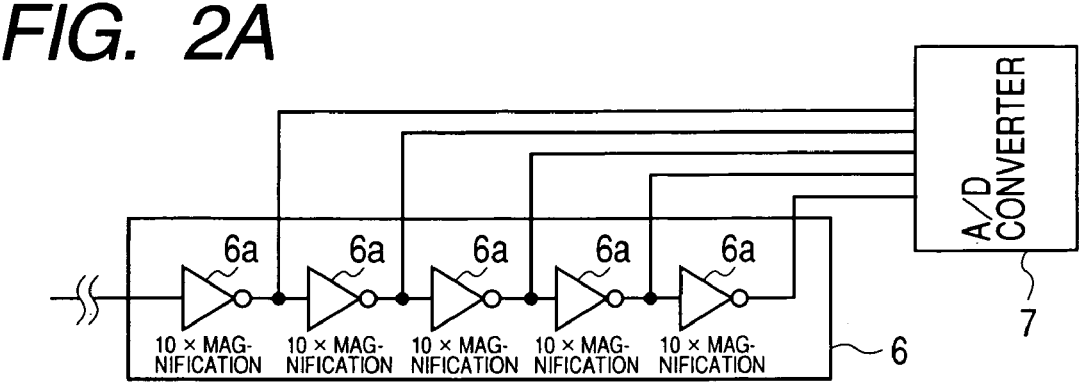
FIGS. 2A, 2B and 2C show examples of an amplifier circuit 6 shown in FIG. 1.
Figure 2B:
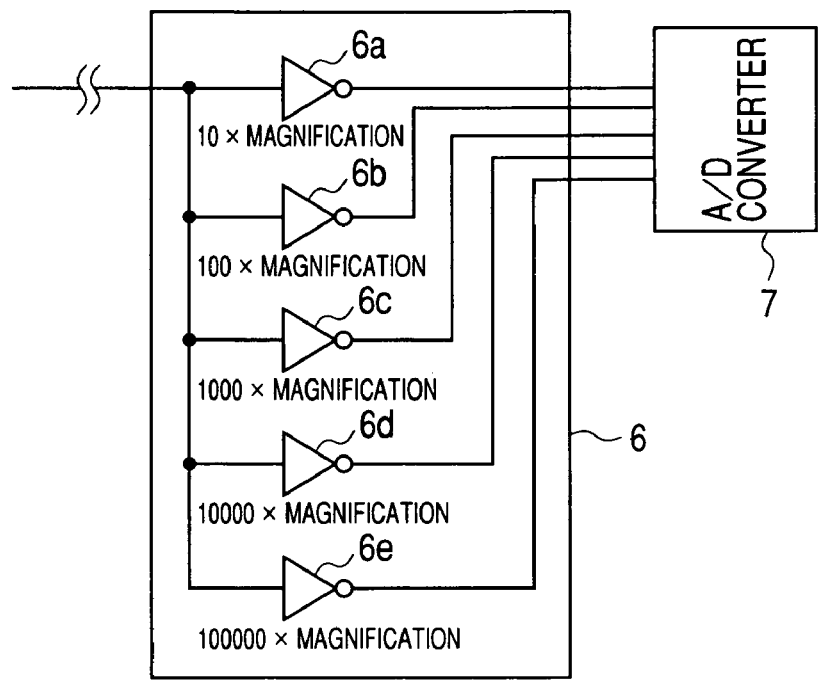
Figure 2C:
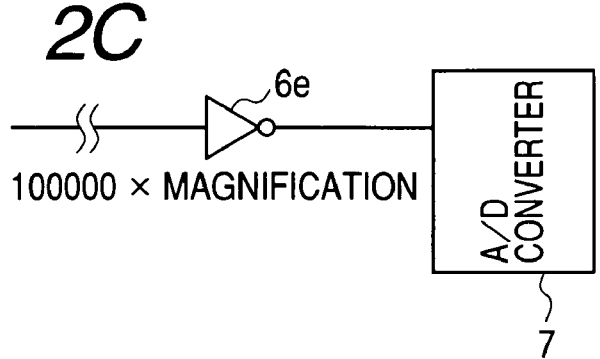

Circuit examples of the amplifier circuit 6 will now be described with reference to the drawings. FIGS. 2A, 2B and 2C show the circuit examples of the amplifier circuit 6 shown in FIG. 1. As shown in FIG. 2A, the amplifier circuit 6 is of a construction in which a plurality of amplifiers 6a (of which the amplification degree is 10 times) are series-connected in multiple stages to thereby amplify the received signal. Also, the output stage of each amplifier 6a is input to the A-D converter 7.

Also, as shown in FIG. 2B, the amplifier circuit 6 is of a construction in which a plurality of amplifiers 6a–6e differing in amplification factor from one another are parallel-connected to thereby amplify the received signal. Also, the outputs of the amplifiers 6a–6e are input to the A-D converter 7.

Also, the amplifier circuit 6 shown in FIG. 2C is of a construction in which a single amplifier 6e of a high amplification factor is used to amplify the received signal. Also, the output of the amplifier 6e is input to the A-D converter 7.

Figure 3:
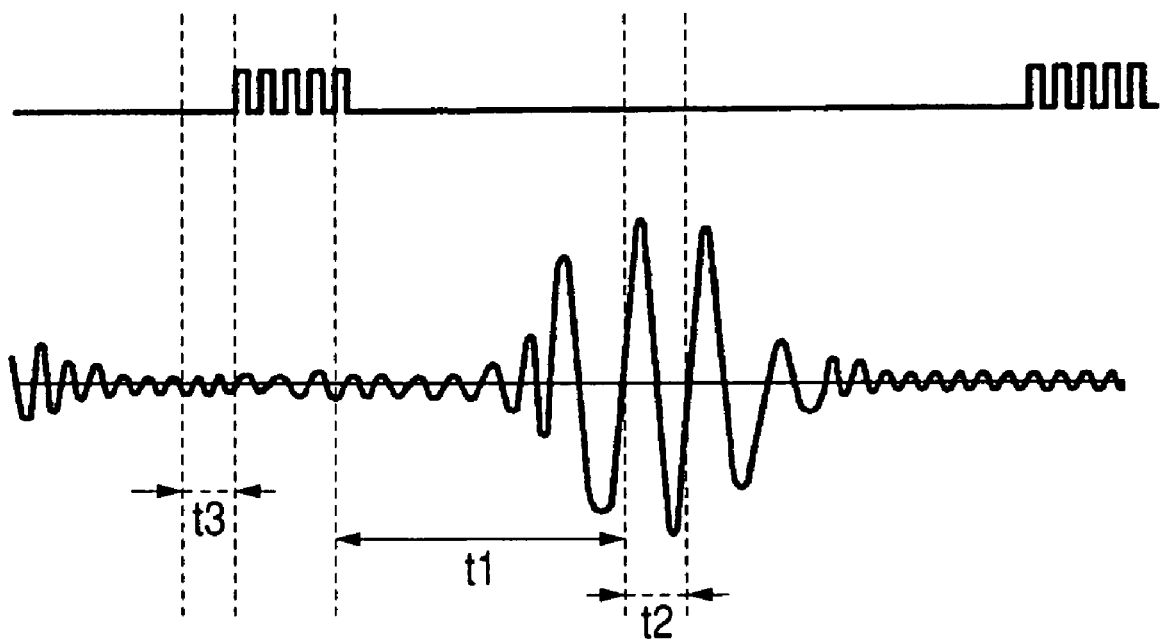
FIG. 3 shows a waveform example of an ultrasonic transmitted by an ultrasonic transmitter 2 shown in FIG. 1 and a waveform example of an ultrasonic received by an ultrasonic receiver 3.

A waveform example of the ultrasonic transmitted by the ultrasonic transmitter 2 and a waveform example of the ultrasonic received by the ultrasonic receiver 3 will now be described with reference to the drawings. FIG. 3 shows a waveform example of the ultrasonic transmitted by the ultrasonic transmitter 2 shown in FIG. 1 and a waveform example of the ultrasonic received by the ultrasonic receiver 3. In FIG. 3, t1 indicates the time from after the ultrasonic is transmitted until it is received. Here, describing a method of calculating t1, the time $t1=d/340$ [s] is calculated from the distance d [m] between the ultrasonic transmitter 2 and the ultrasonic receiver 3, and the propagation speed 340 [m/s] of the ultrasonic. Thereby, in a time $t=t1$ [s] after the last ultrasonic pulse has been transmitted from the ultrasonic transmitter 2; the received signal is received by the ultrasonic receiver 3.

As shown above, the time t [s] is calculated before the transport of the paper 1, and at the time t, the received ultrasonic signal output by the ultrasonic receiver 3 is sampled by the A-D converter 7, whereby it becomes possible to obtain the vicinity of the maximum value of the ultrasonic signal intensity. There is a case where after the ultrasonic signal has been transmitted, the reverberation of the ultrasonic remains in the transport path for the paper 1 depending on the construction of the apparatus, and the maximum value of the ultrasonic signal intensity is assumed a little later after the time t [s] found by the above-described calculation and therefore, in such case, it is necessary to estimate the time t [s] longer by a half period to about a period of the ultrasonic waveform.

Also, t2 in FIG. 3 indicates a range within which the sampling of the received ultrasonic signal is performed. Since it is necessary that the maximum value and minimum value at the amplitude of the ultrasonic signal be included in the waveform information of the received ultrasonic signal obtained by the ultrasonic receiver 3, the A-D converter 7 performs sampling within the range of a period of the received ultrasonic signal, and obtains the received ultrasonic signal. Assuming here that a period is t2 [s] and the number of sampling points obtained from a period is n, the time when the ith sampling point is received by the ultrasonic receiver 3 is $t=t1+(t2 \times i/n)$ [s] after the ultrasonic signal is transmitted.

Also, besides the ultrasonic signal transmitted from the ultrasonic transmitter 2, a noise signal from an external device enters the ultrasonic receiver 3 and therefore, a time average is done to thereby reduce the noise signal. The above-mentioned time average is, for example, a value found by obtaining sample values at eight times to thereby calculate an average value. However, in order to avoid a situation in which the time average including a spike noise by static electricity or the like is done, when as compared with a signal amplitude obtained at the last time at the same sampling point, the value is greatly fluctuated, that value is prevented from being included in the time interval of the ultrasonic signal.

In FIG. 3, t3 indicates the timing at which the ultrasonic receiver 3 effects the obtainment of a noise signal waveform. As indicated by t3 in FIG. 3, during the time t=t3 [s] after the attenuation of the ultrasonic signal and before the transmission of the next ultrasonic pulse, signal information is obtained from the ultrasonic receiver 3, whereby it is possible to obtain a noise signal (herein, an ultrasonic signal remaining as reverberation in the paper transport path after the transmission of the ultrasonic has ended) in a state in which the influence of the ultrasonic is little. Thus, the double feed detecting apparatus 10 using an ultrasonic becomes capable of grasping the level of the noise signal in accordance with changes in the environment in an apparatus wherein the double feed detecting apparatus is incorporated, the amplification factor of the amplifier circuit 6, etc., and performing the double feed detection by the level determining process.

The function of the control circuit 4 of FIG. 1 will be described here with reference to the drawings.

Figure 4:
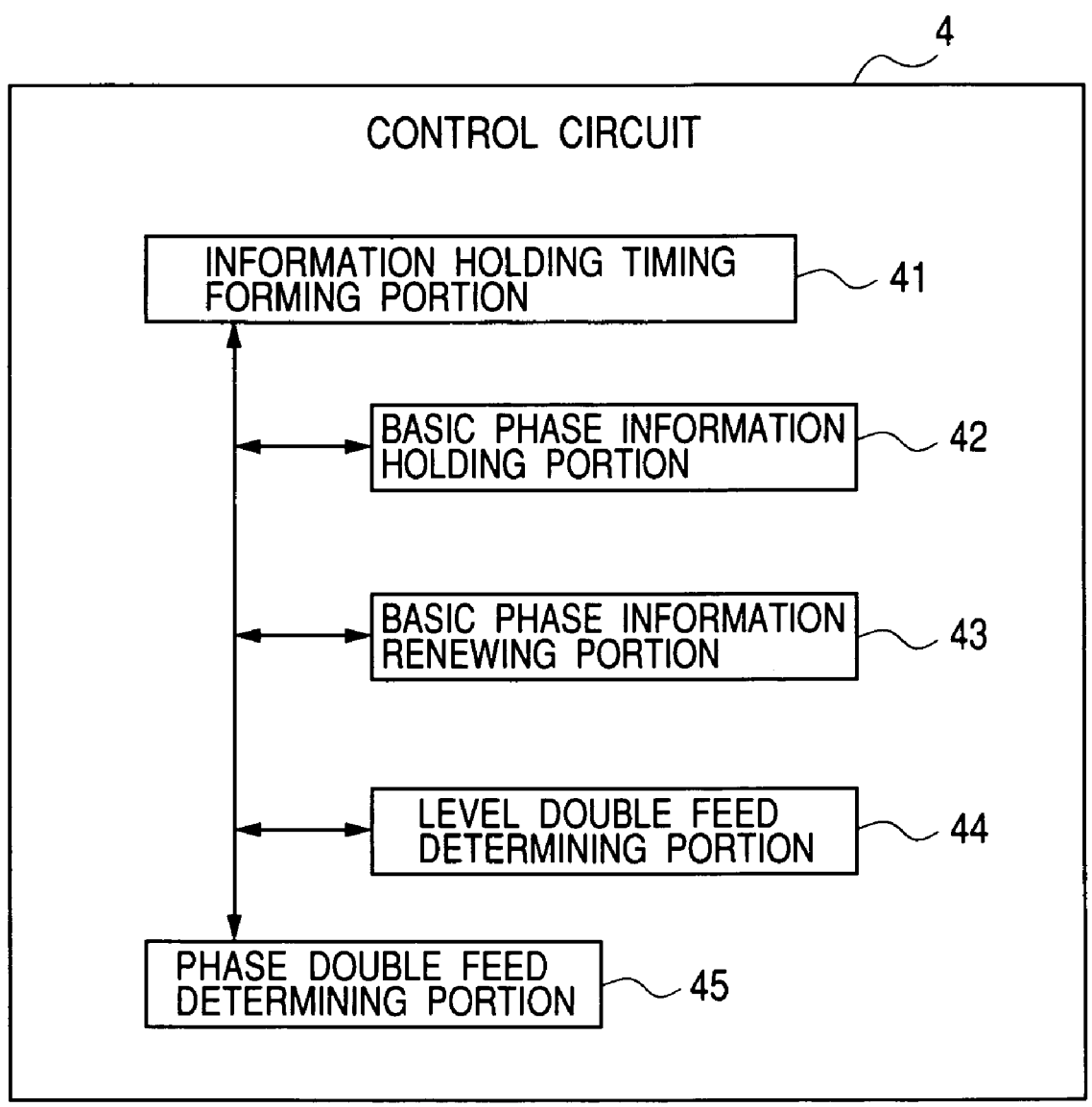
FIG. 4 is a block diagram schematically showing functions provided in a control circuit 4 shown in FIG. 1.

FIG. 4 is a block diagram showing the epitome of the function of the control circuit shown in FIG. 1. In FIG. 4, the reference numeral 41 designates an information holding timing forming portion which forms a timing signal for obtaining a basic phase which is the reference of a phase when double feed detection is performed by a phase determining process. Specifically, the information holding timing forming portion 41 monitors the attenuation of the amplifier of the received ultrasonic signal received by the ultrasonic receiver 3, and forms a timing signal if the attenuation is attenuation below a predetermined threshold value (the absence of the interception of the ultrasonic by the paper 1). The reference numeral 42 denotes a basic phase information holding portion which holds phase information obtained before the attenuation of the received ultrasonic signal as basic phase information in accordance with the timing signal formed by the information holding timing forming portion 41. The reference numeral 43 designates a basic phase information renewing portion which carries out the process of renewing the basic phase information held by the basic phase information holding portion 42. The reference numeral 44 denotes a level double feed determining portion which performs the detection of double feed by the level determining process. The reference numeral 45 designates a phase double feed determining portion which performs the detection of double feed by the phase determining process. The detailed operations of the respective processing portions shown in FIG. 4 will be described later.

By the above-described construction, the double feed detecting apparatus 10 which is an embodiment of the present invention can obtain the following effects, as compared with the conventional apparatus.

In the double feed detection by the conventional level determining process, when as compared with the reception intensity in a normal transport state, double feed occurred, the fact that the received ultrasonic signal is greatly attenuated was utilized to set a certain constant value added to the ultrasonic reception intensity during the occurrence of double feed as a threshold value, and if the intensity of the received ultrasonic became equal to or less than the threshold value, it was judged as double feed. However, external factors change or the amplification factor of the amplifier circuit 6 is changed by the unevenness of the performance of constituent electrical parts to thereby cause a fluctuation in reception intensity and therefore, there was the undesirable possibility of the accuracy of double feed detection being reduced. In contrast, in the level determining process of the present invention, the level double feed determining portions 44 finds the ratio (SN ratio) between the amplitude value S at the maximum reception intensity of the ultrasonic signal and the amplitude value N of the noise signal (herein, the reverberation of the ultrasonic after the attenuation of the ultrasonic signal), and if the value (S/N) thereof becomes equal to or less than 1.5, it is judged as double feed. Thereby, even if there occurs the fluctuation of the external factors or the amplification factor, it does not affect the SN ratio and therefore, there is obtained the effect that the accuracy of double feed detection is not reduced. When the SN ratio is to be found, the amplitude of the noise signal may be made as great as a constant.

Description will now be made of the phase determining process in the double feed detecting apparatus 10 according to the present embodiment.

The phase of the ultrasonic signal transmitted through double-fed paper causes a great difference as compared with the basic phase and therefore, the phase determining process is used for the detection of the double feed of paper which could not be detected by the level determining process, or the detection of the double feed of paper transported while closely adhering due to static electricity, an adhesive agent or the like. The double feed detecting apparatus 10 according to the present embodiment uses the phase determining process in addition to the above-described level determining process, whereby it can further improve the accuracy of double feed detection and can prevent the omission of double feed detection.

Figure 5:
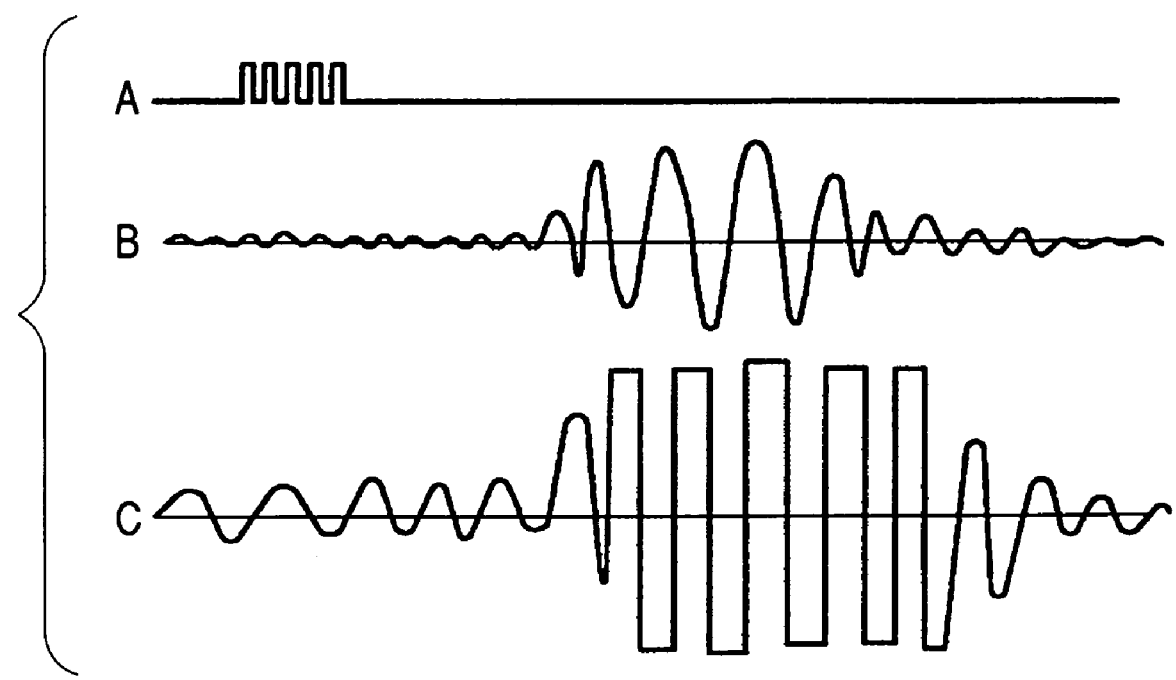
FIG. 5 shows waveform examples of a received ultrasonic signal during amplification (before saturation) and after amplification (after saturation) used for fixing a basic phase when double feed is detected by a phase determining process.

FIG. 5 shows waveform examples of the received ultrasonic signal during amplification (before saturation) and after amplification (after saturation) which are used for the fixing of the basic phase when double feed is detected by the phase determining process. The waveform A of FIG. 5 shows the waveform of an ultrasonic pulse transmitted from the ultrasonic transmitter 2. The waveform B of FIG. 5 is a waveform showing the received ultrasonic signal input from the ultrasonic receiver 3 to the amplifier circuit 6 and being at a stage in the course of amplification. The waveform C of FIG. 5 is a waveform showing the received ultrasonic signal input from the ultrasonic receiver 3 to the amplifier circuit 6 and amplified until saturated.

As the basic phase information used for the double feed detection by the phase determining process, use is made of the phase information of the ultrasonic signal when the paper (sheet material) 1 begins to intercept the ultrasonic. However, the received ultrasonic signal amplified until its waveform is saturated like the waveform C of FIG. 5 cannot catch the beginning of the interception by the paper (sheet material) 1. So, by using the received signal at a stage whereat it is not yet saturated which is being amplified and sensitively responds to the beginning of the interception by the paper (sheet material) 1, as indicated by the waveform B of FIG. 5, it becomes possible to catch the beginning of the interception by the leading edge portion of the paper (sheet material) 1.

Changes in the environment occur due to changes in the ambient temperature, humidity and the atmospheric pressure, the vibration by the transport of the paper 1 and the opening and closing operation of the unit and therefore, the basic phase (the phase of the received ultrasonic signal obtained in the absence of the paper between the ultrasonic transmitter 2 and the ultrasonic receiver 3) is renewed each time the paper is transported.

Figure 6:
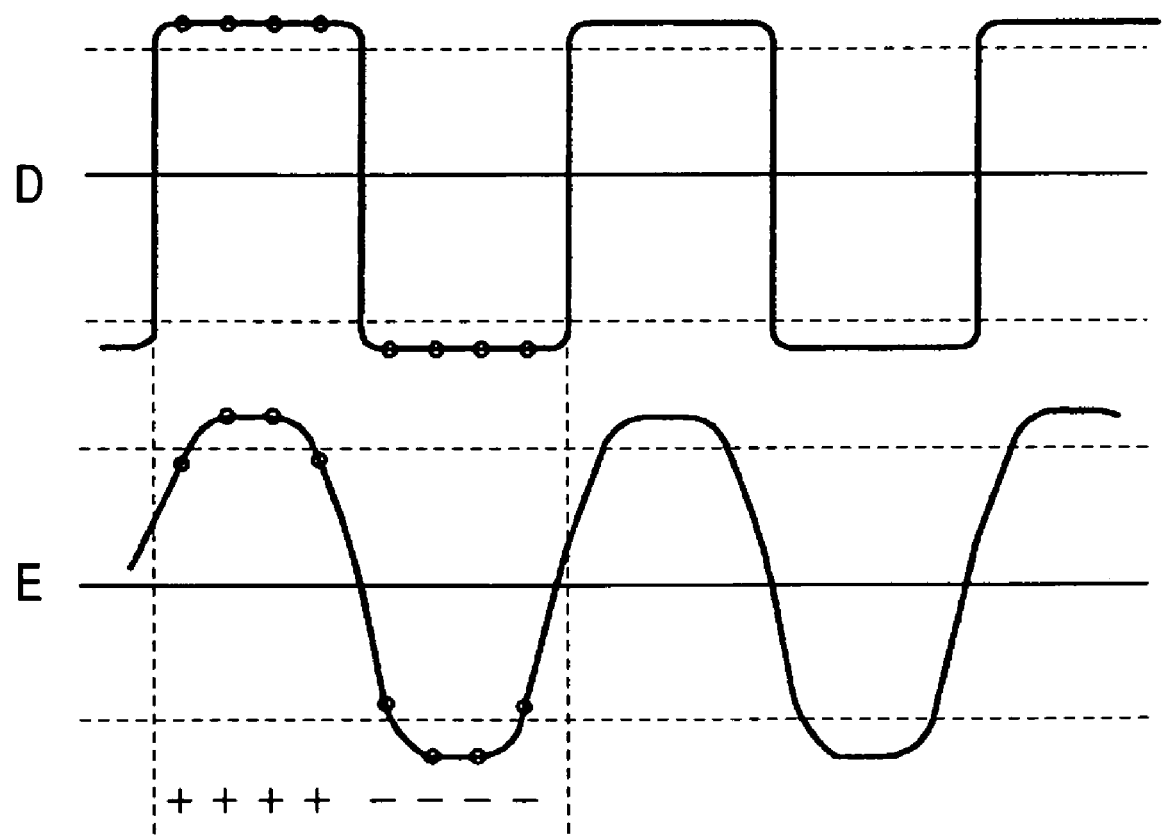
FIG. 6 shows a technique of monitoring the received ultrasonic signal amplified by the amplifier circuit 6 until it is saturated as indicated by a waveform C in FIG. 5, and obtaining basic phase information.

FIG. 6 shows the information holding time in a case where as shown in FIG. 2C, the amplifier circuit 6 is comprised of a single amplifier having a high amplification factor, and also shows a technique of monitoring the received ultrasonic signal amplified by the amplifier circuit 6 until saturated as shown by the waveform C of FIG. 5, and obtaining the basic phase information. When the paper 1 begins to come into between the ultrasonic transmitter 2 and the ultrasonic receiver 3 (hereinafter referred to as between the ultrasonic sensors), the reception intensity is attenuated and like the waveform D of FIG. 6, the amplitude becomes small as compared with the saturated portion of the waveform C of FIG. 5. Further, when the paper 1 is moved to thereby intercept the ultrasonic, a portion not saturated is formed in the waveform, as indicated by the waveform E of FIG. 6. In the present embodiment, the information holding timing forming portion 41 transmits a timing signal at the point of time of the waveform E of FIG. 6 whereat four of eight sampling points have come out of a saturated state. Thereby, the basic phase information renewing portion 43 causes the phase information obtained before the saturation of the received ultrasonic signal to be held as the basic phase information in the basic phase information holding portion 42. The description of the present embodiment, however, is not meant to be restricted to what describes the control of a signal intensity changing device and each set value.

Figure 7:
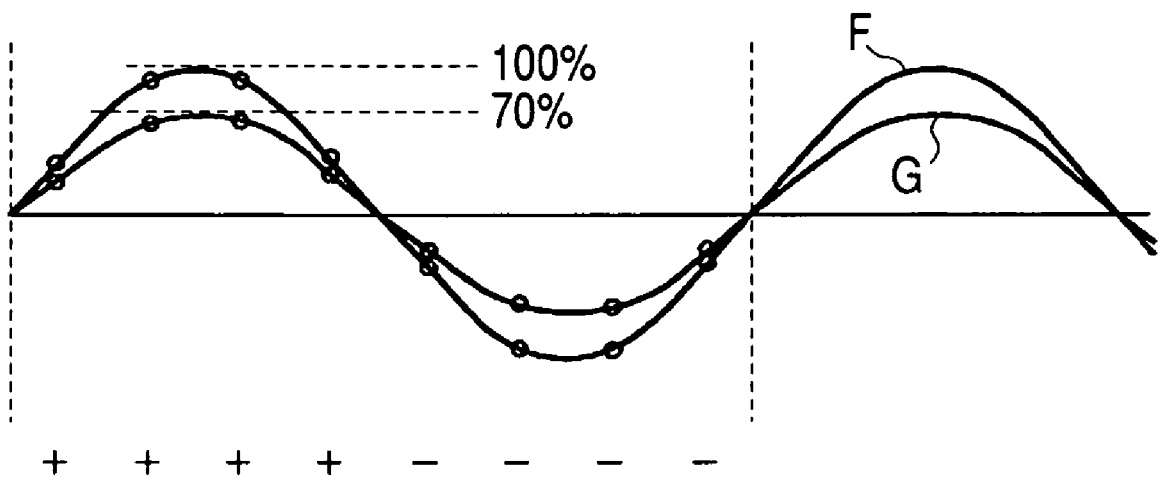
FIG. 7 shows a technique of monitoring the received ultrasonic signal amplified up to an intermediate stage by the amplifier circuit 6 as indicated by a waveform B in FIG. 5, and obtaining basic phase information.

FIG. 7 shows the information holding timing in a case where the amplifier circuit 6, as shown in FIGS. 2A and 2B, is comprised of a plurality of amplifiers having a plurality of amplification factors, and also shows a technique of monitoring the received ultrasonic signal amplified to an intermediate stage by the amplifier circuit 6 as indicated by the waveform B of FIG. 5, and obtaining the basic phase information. A received waveform having a large reception amplitude, as indicated by the waveform F of FIG. 7, is in a state in which there is no interceptor (paper 1) between the ultrasonic sensors, and a received waveform having a small reception amplitude, as indicated by the waveform G of FIG. 7, is in a state in which the interceptor (paper 1) has begun to come into between the ultrasonic sensors.

The information holding timing forming portion 41 monitors the number of the saturated sampling points in the waveform D of FIG. 6, and at a stage whereat four of the eight sampling points have come out of the saturated state (the waveform E of FIG. 6), it judges that the interceptor (paper 1) has begun to come into between the ultrasonic sensors, and forms a timing signal, and forms a timing signal.

Alternatively, the information holding timing forming portion 41 monitors whether the signal amplitude of the waveform F of FIG. 7 changes, and if the signal amplitude changes, it compares that signal amplitude with the amplitude of the received ultrasonic signal (the waveform F of FIG. 7) under a condition in which the interceptor (paper 1) is absent between the ultrasonic sensors. In the present embodiment, the information holding timing forming portion 41 judges at a stage (the waveform G of FIG. 7) whereat the amplitude of the received ultrasonic signal has been attenuated to 70% of the waveform F that the interceptor (paper 1) has begun to come into between the ultrasonic sensors, and forms a timing signal.

Also, the basic phase information renewing portion 43 holds in the basic phase information holding portion 42 the phase information of the waveform of the received ultrasonic signal after amplification (after saturation) indicated by the waveform D of FIG. 6 and obtained by the amplifier circuit 6 before the interceptor (paper 1) begins to come into between the ultrasonic sensors, in accordance with the formed timing signal. Here, the held phase information provides the basic phase information. The description of the present embodiment, however, is not meant to be restricted to what describes the control of the signal intensity changing device and each set value.

Figure 8:
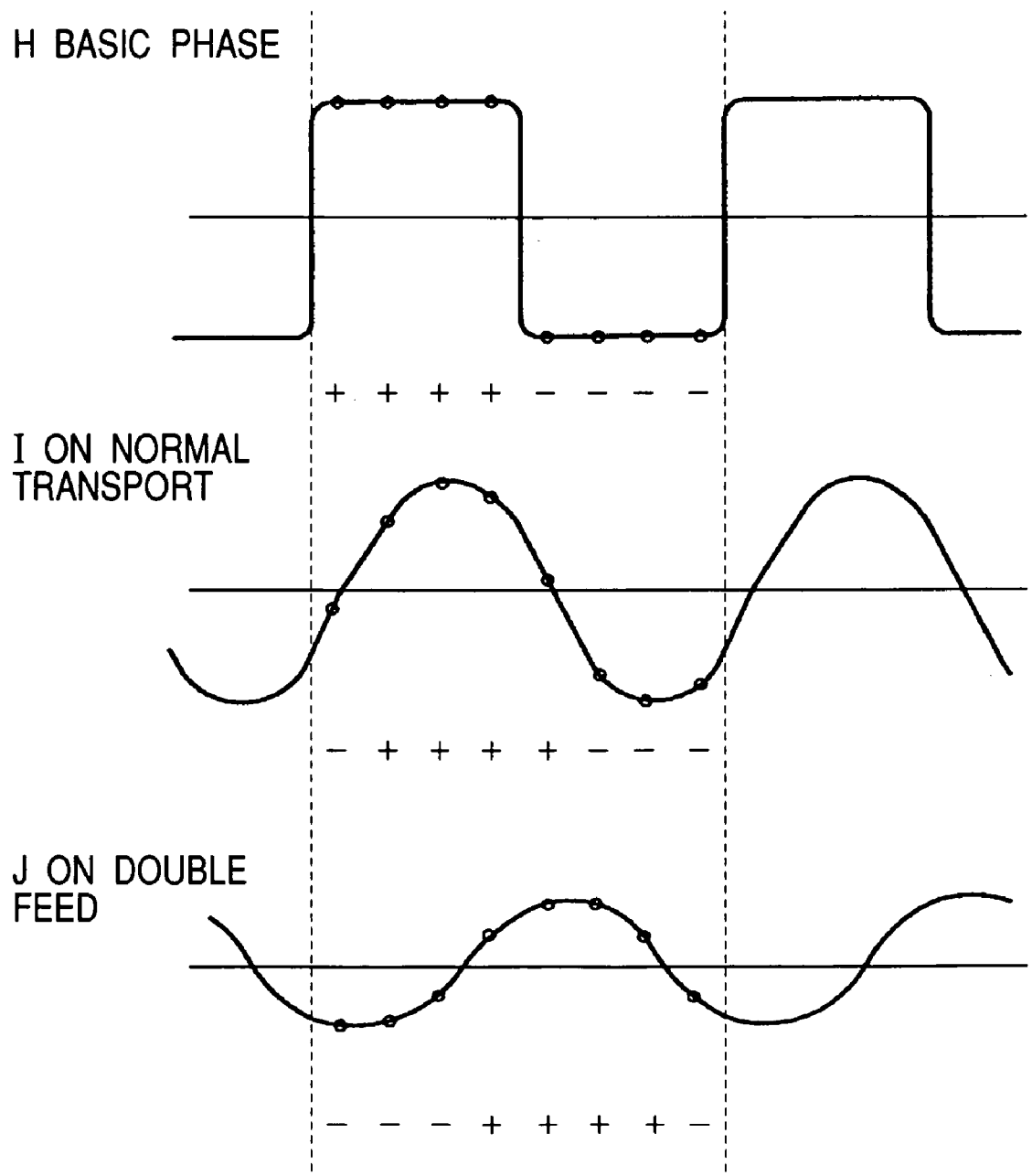
FIG. 8 shows a waveform example of a basic phase in the present embodiment, and waveform examples on normal transport and on double feed.

FIG. 8 shows a waveform example of the basic phase in the present embodiment, and waveform examples on normal transport and on double feed. The waveform H of FIG. 8 indicates the waveform of the received ultrasonic signal during the obtainment of the basic phase information. The waveform I of FIG. 8 indicates the waveform of the received ultrasonic signal on normal transport (on the transport of a sheet of paper 1). The waveform J of FIG. 8 indicates the waveform of the received ultrasonic signal on double feed. As shown in FIG. 8, the waveform on the normal transport of the paper 1 (the waveform I of FIG. 8), as compared with the waveform H, is small in both of the attenuation of signal intensity and phase change, and the waveform on the double feed of the paper 1 (the waveform J of FIG. 8), as compared with the waveform H, is great in both of the attenuation of signal intensity and phase change.

In the present embodiment, as indicated by marks on the waveforms, there are eight sampling points in one period of the received ultrasonic signal, and the each sampling point is given the sign of + or −. When four or more of these signs change as compared with the basic phase, the phase double feed determining portion 45 judges by the change in phase information that the paper is being double-fed. The description of the present embodiment, however, is not meant to be restricted to what describes each set value.

Description will now be made of the operation of the double feed detecting apparatus 10 shown in FIG. 1.

Figure 9:
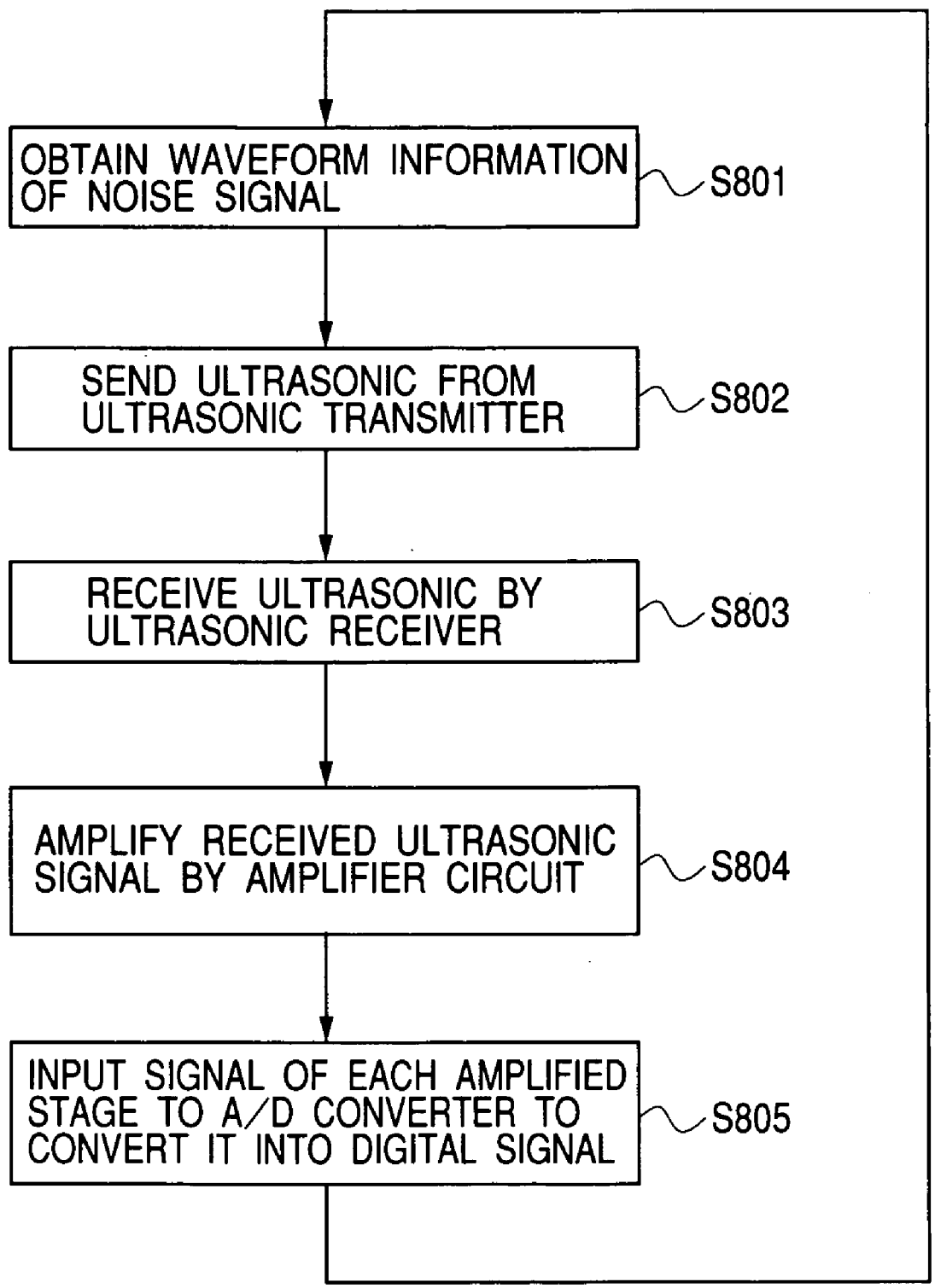
FIG. 9 is a flow chart showing operations from the transmission of an ultrasonic signal by the double feed detecting apparatus 10 shown in FIG. 1 to the reception of the signal, the amplification of the signal and the conversion of the signal.

FIG. 9 is a flow chart showing the operation of the double feed detecting apparatus 10 shown in FIG. 1 from the transmission of the ultrasonic signal to the reception of the signal, the amplification of the signal and the conversion of the signal. As shown in FIG. 9, at a step S801, the ultrasonic receiver 3 obtains a noise signal (the attenuated wave of the ultrasonic transmitted at the last time immediately before an ultrasonic is transmitted from the ultrasonic transmitter 2. Next, at a step S802, the ultrasonic transmitter 2 transmits an ultrasonic. Next, at a step S803, the ultrasonic receiver 3 receives the ultrasonic in a constant time (a time t1 calculated from the distance d between the ultrasonic transmitter 2 and the ultrasonic receiver 3) after the sending of the ultrasonic.

Next, since the ultrasonic received by the ultrasonic receiver 3 has been attenuated by the influence of the propagation thereof through the space or the transmission thereof through the paper 1, the amplitude of the received ultrasonic signal is not sufficient, and at a step S804, the amplifier circuit 6 performs the amplification of the signal. Next, an analog signal output from each amplifying stage of the amplifier circuit 6 is input to the A-D converter 7, and at a step S805, the A-D converter 7 samples the input analog signal (amplified received ultrasonic signal) and converts it into a digital signal which can be processed by the control circuit 4. Also, when the processing of the step S805 is ended, return is made to the step S801. Thus, the double feed detecting apparatus 10 processes the digital signal of the received ultrasonic signal received by the ultrasonic receiver 3, by the control circuit 4, thereby detecting whether the paper 1 is being double-fed or not.

Description will now be made of the double feed determining process carried in the control circuit 4 on the basis of the digital signal after converted by the A-D converter 7 as described above.

Figure 10:
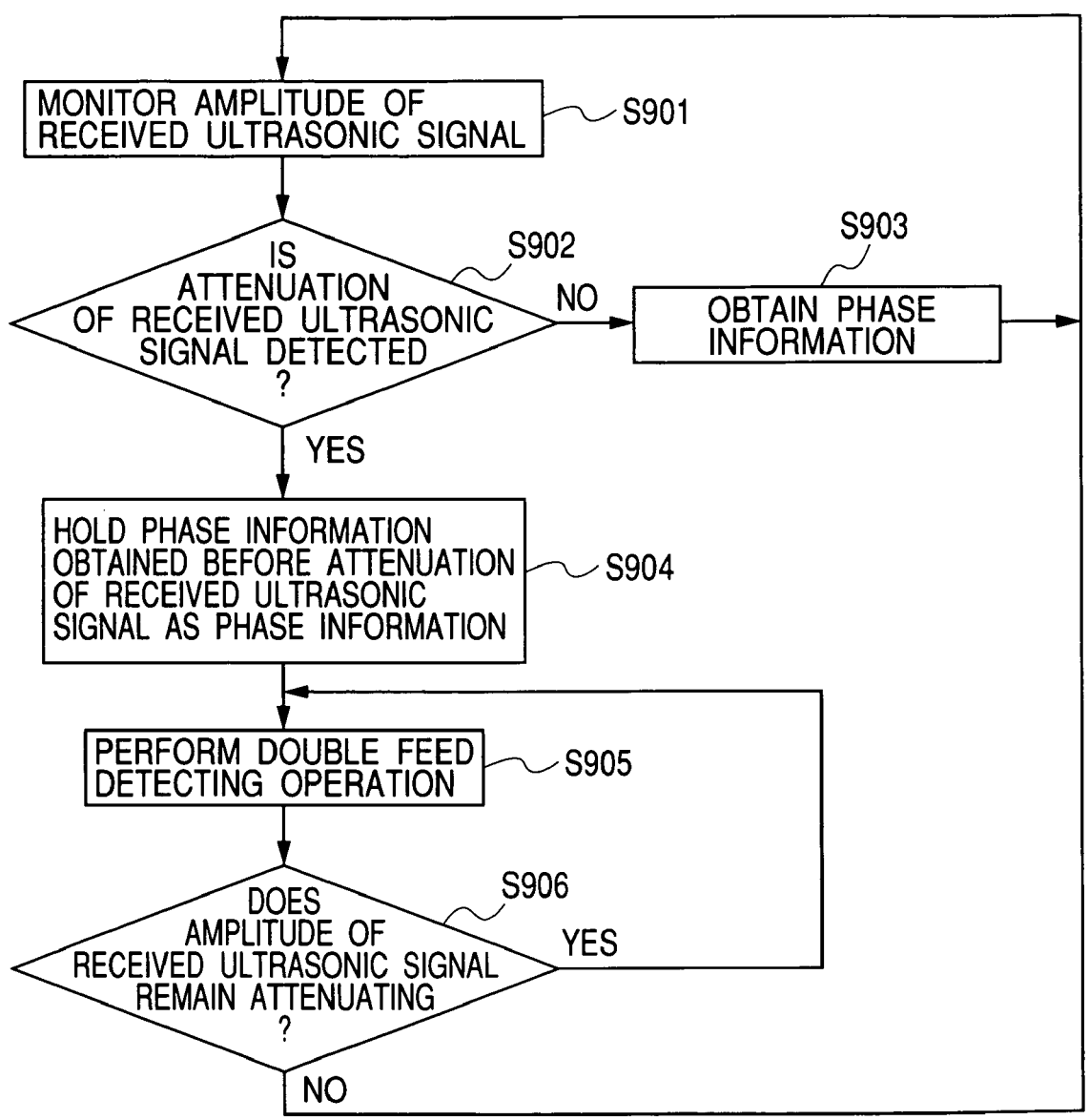
FIG. 10 is a flow chart showing a process in which the control circuit 4 renews and hold the basic phase information used for double feed determination by phase in a basic phase information holding portion 42.

FIG. 10 is a flow chart showing the process in which the control circuit 4 renews and holds the basic phase information used for the double feed determination by phase in the basic phase information holding portion 42. As shown in FIG. 10, first at a step S901, the information holding timing forming portion 41 of the control circuit 4 monitors the attenuation of the amplitude of the received ultrasonic signal. Specifically, the information holding timing forming portion 41 detects a change in which the amplitude attenuates from the waveform D of FIG. 6 to the waveform E, and a change in which the amplitude attenuates from the waveform F of FIG. 7 to the waveform G.

Here, when the received ultrasonic signal does not attenuate (NO at a step S902), at a step S903, the basic phase information renewing portion 43 obtains as phase information the waveform of the received ultrasonic signal in its saturated state as indicated by the waveform D of FIG. 6. Also, when the attenuation of the received ultrasonic signal is detected (YES at the step S902), at a step S904, phase information obtained before the attenuation of the received ultrasonic signal is held as basic phase information in the basic phase information holding portion 42. Next, at a step S905, a double feed detecting operation is performed by the use of the held basic phase information. If the amplitude of the received ultrasonic signal remains attenuating (YES at a step S906), the double feed detecting operation is again performed at the step S905. When NO at the above-described step S903 and step S906 is ended, return is made to the step S901.

Description will now be made of the operation of the control circuit 4 performing double feed detection on the basis of the digitized received ultrasonic signal input from the A-D converter 7.

Figure 11:
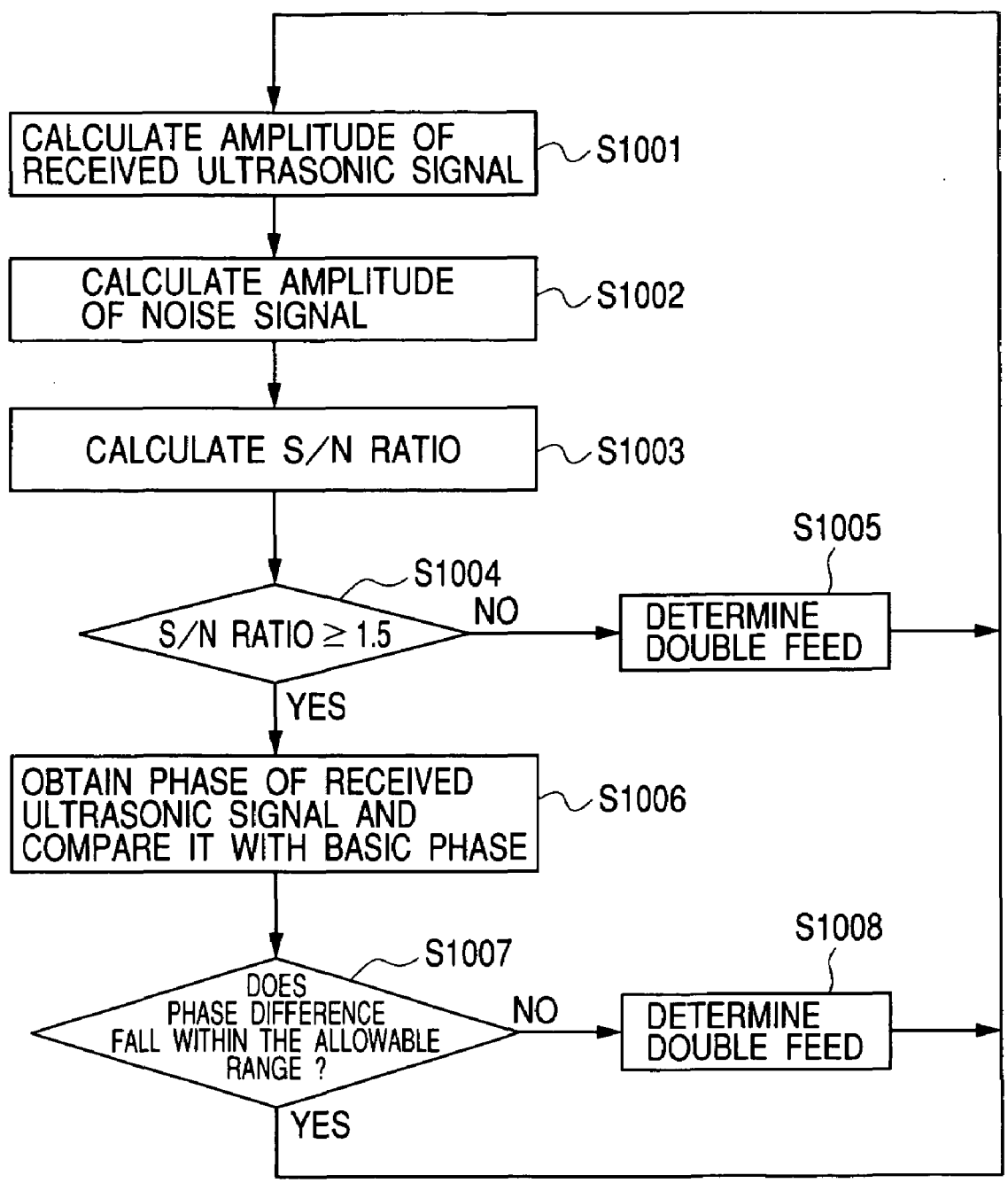
FIG. 11 is a flow chart showing an operation in which the control circuit 4 shown in FIG. 1 performs double feed detection.

FIG. 11 is a flow chart showing the operation of the control circuit 4 shown in FIG. 1 performing double feed detection. As shown in FIG. 11, first at a step S1001, the level double feed determining portion 44 calculates the amplitude of the received ultrasonic signal obtained at the timing of t2 in FIG. 3. Next, at a step S1002, the level double feed determining portion 44 calculates the amplitude of the noise signal obtained at the timing of t3 in FIG. 3. Next, at a step S1003, the level double feed determining portion 44 calculates the SN ratio (the ratio between the amplitude of the received ultrasonic signal and the amplitude of the noise signal) by the level determining process on the basis of the amplitude of the received ultrasonic signal calculated at the step 1001 and the amplitude of the noise signal.

Next, at a step S1004, the level double feed determining portion 44 compares the value of the calculated SN ratio with a prescribed value (1.5 in the present embodiment). If the value of the SN ratio is less than the prescribed value (NO at the step S1004), advance is made to a step S1005, where the level double feed determining portion 44 determines double feed, and outputs to the effect that the double feed of the paper 1 has been detected. Also, if the value of the SN ratio is equal to or greater than the prescribed value (that is, double feed has not been determined by the level determining process) (YES at the step S1004), advance is made to a step S1006, where the phase double feed determining portion 45 compares the phase of the obtained received ultrasonic signal with the basic phase by the phase determining process.

If as the result of this comparison, the phase difference between the basic phase and the phase of the received ultrasonic signal is outside the allowable range (NO at a step S1007), advance is made to a step S1008, where the phase double feed determining portion 45 determines double feed, and outputs to the effect that the double feed of the paper 1 has been detected. In the present embodiment, it is to be understood that when as described in connection with FIG. 8, among the sampling number of a period, the sign of a prescribed number or greater (in FIG. 8, the prescribed number is 4 for the sampling number 8) differs, the phase difference is outside the allowable range. Also, if the phase difference between the basic phase and the phase of the received ultrasonic signal is within the allowable range (YES at the step S1007), return is made to the step S1001.

As shown above, according to the double feed detecting apparatus 10 of the present embodiment, even when for example, the paper 1 is thin and therefore, in spite of double feed, the double feed cannot be determined by the level determining process, accurate double feed detection can be accomplished by the use of the phase determining process. Also in the level determining process, according to the double feed detecting apparatus 10 of the present embodiment, use is made of the SN ratio which is the ratio between the amplitude of the received ultrasonic signal and the amplitude of the noise signal and therefore, even if the external factors such as the distance between the sensors, the thickness of the sheet material, the ambient temperature and humidity and the atmospheric pressure change, double feed can be detected accurately.

Also, each processing portion shown in FIG. 4 may be what is realized by hardware for exclusive use, and each processing portion may be what is comprised of a memory and a central processing unit (CPU) in the control circuit 4, and reads a program for realizing the function of each processing portion into the memory and executes it to thereby realize the function thereof.

Also, it is to be understood that the above-mentioned memory is comprised of a hard disc device, a magneto-optical disc device, a nonvolatile memory such as a flash memory, a recording medium such as a CD-ROM capable of reading only, a volatile memory like a random access memory (RAM) or a recording medium capable of computer-reading and writing by a combination of these.

Also, a program for realizing the functions of the processing portions for carrying out various processes in FIG. 4 may be recorded in a recording medium capable of computer-reading, and the program recorded in this recording medium may be read into the CPU in the control circuit 4 and be executed to thereby carry out each process.

Also, the "recording medium capable of computer-reading" refers to a portable medium such as a flexible disc, a magneto-optical disc, a ROM or a CD-ROM, or a storage device such as a hard disc contained in a computer system. Further, it is to be understood that the "recording medium capable of computer-reading" also includes what holds a program for a constant time, like a volatile memory (RAM) in the CPU in the control circuit 4 which becomes a server or a client when a program is sent through a network such as the Internet or a communication circuit such as a telephone circuit.

Also, the above-mentioned program may be sent from a computer system storing this program in a memory or the like to the memory in the control circuit 4 through a transmitting medium or by a transmitting wave in the transmitting medium. Here, the "transmitting medium" for transmitting the program refers to a medium having the function of transmitting information like a network (communication net) such as the Internet or a communication circuit (communication line) such as a telephone circuit.

Also, the above-mentioned program may be that for realizing part of the aforedescribed function. Further, it may be what can realize the aforedescribed function by the combination thereof with a program already recorded in the memory in the control circuit 4, i.e., a so-called differential file (differential program).

Also, a program product such as a computer-readable recording medium having the above-mentioned program recorded therein can be applied as an embodiment of the present invention.

The adjustment of the signal intensity of the received ultrasonic signal will now be described. When performing double feed detection by the use of an ultrasonic, differences in signal amplification factor and resonance frequency occur to each product due to the unevenness of the characteristics of the ultrasonic transmitter 2 and the ultrasonic receiver 3, and the unevenness of the constituent parts of the amplifier circuit 6. Accordingly, a transmitting method and a receiving method for the ultrasonic must be controlled to thereby properly adjust the signal intensity of the received ultrasonic signal.

Figure 12A:
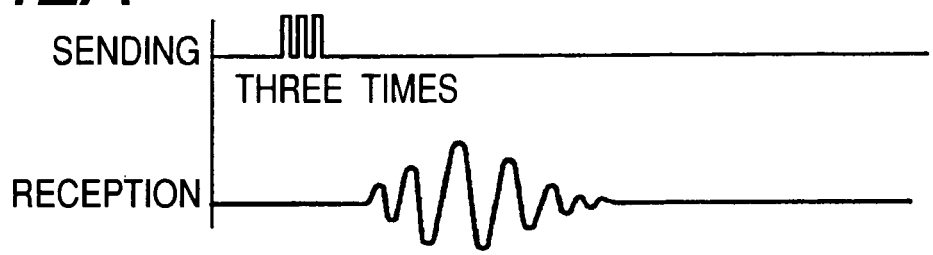
FIGS. 12A, 12B and 12C show changes in the signal intensity of the received ultrasonic signal by changes in the pulse number of an ultrasonic signal.
Figure 12B:
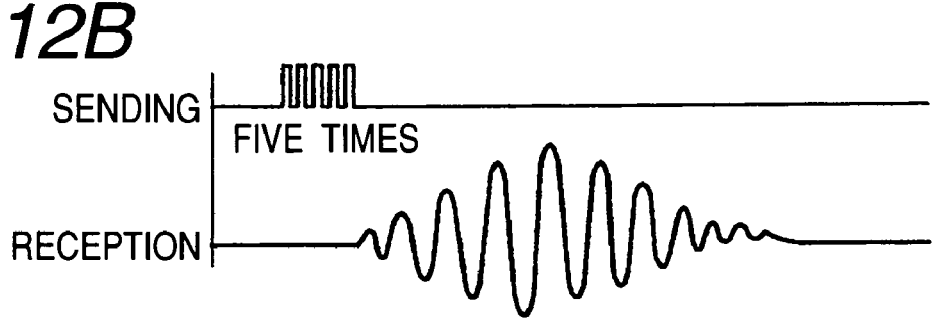
Figure 12C:
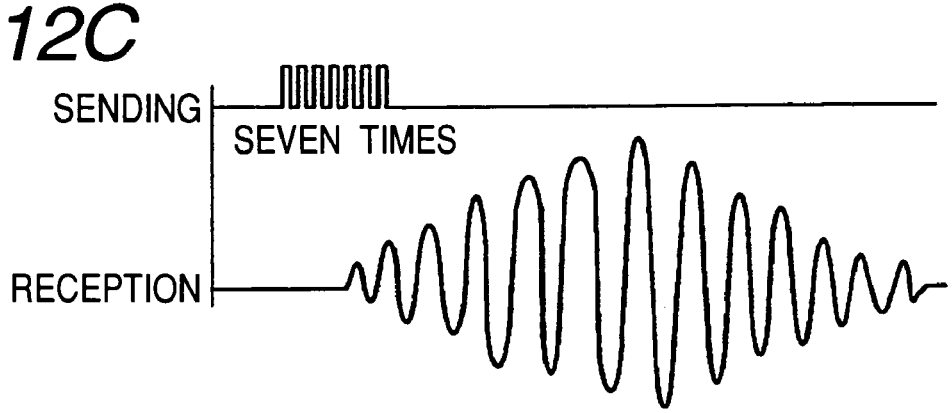

So, as an embodiment of an adjusting method in the signal intensity of the received ultrasonic signal, a method by changing the pulse number of the ultrasonic signal will hereinafter be described with reference to FIGS. 12A, 12B and 12C. FIGS. 12A, 12B and 12C show the pulse numbers of times of respective different ultrasonic signals, and the signal intensity of the received ultrasonic signal during the reception of the ultrasonics of those pulse numbers of time.

FIG. 12A shows a change in the signal intensity of the received ultrasonic signal in the ultrasonic receiver 3 when the pulse number of the ultrasonic signal is three times.

FIG. 12B shows a change in the signal intensity of the received ultrasonic signal in the ultrasonic receiver 3 when the pulse number of the ultrasonic signal is five times.

FIG. 12C shows a change in the signal intensity of the received ultrasonic signal in the ultrasonic receiver 3 when the pulse number of the ultrasonic signal is seven times.

As shown in FIGS. 12A, 12B and 12C, in accordance with an increase in the pulse number of the ultrasonic signal, the signal intensity of the received ultrasonic signal also increases. Consequently, the control circuit 4 controls so as to increase the pulse number of the ultrasonic signal when the received ultrasonic signal is smaller than a prescribed value (S2), and so as to decrease the pulse number of the ultrasonic signal when the received ultrasonic signal is greater than the prescribed value (S2). The control circuit 4 repeats the above-described operation of changing the pulse number of the ultrasonic signal a plurality of times to thereby adjust the pulse number so that the signal intensity of the received ultrasonic signal may become most approximate to the prescribed value (S2).

By the above-described control of the pulse number by the control circuit 4, the adjustment of the signal intensity of the received ultrasonic signal by the changing of the pulse number of the ultrasonic signal is effected, whereby even when external factors such as the changing of the thickness of the paper 1 and a rise in temperature which affect the reception of the ultrasonic change, the signal intensity of the received ultrasonic signal can be kept proper and therefore, the accuracy of double feed detection can be prevented from being reduced. That is, the double feed detecting apparatus 10 according to the present embodiment can control the pulse number of the ultrasonic signal to thereby properly adjust the signal intensity of the received ultrasonic signal received by the ultrasonic receiver 3, and prevent a reduction in the accuracy of double feed detection caused by changes in the external factors.

As another embodiment, description will now be made of a method of adjusting the signal intensity of the received ultrasonic signal in the ultrasonic receiver 3 by the control circuit 4 changing the pulse amplitude of the ultrasonic signal.

Figure 13A:
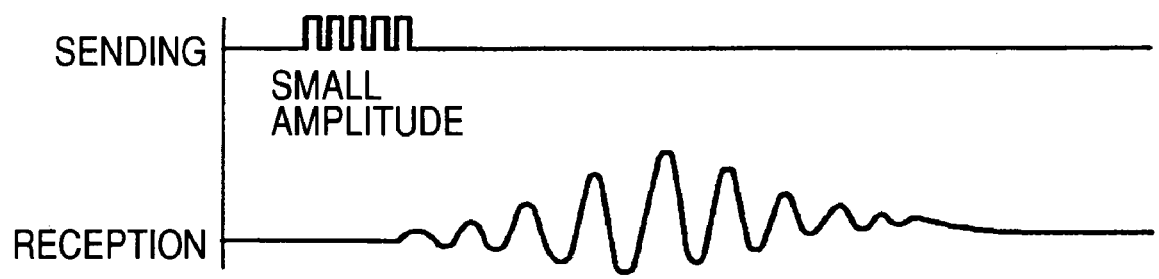
FIGS. 13A and 13B show that the signal intensity of the received ultrasonic signal in the ultrasonic receiver 3 changes in accordance with a change in the pulse amplitude of the ultrasonic signal output by the control circuit 4.
Figure 13B:
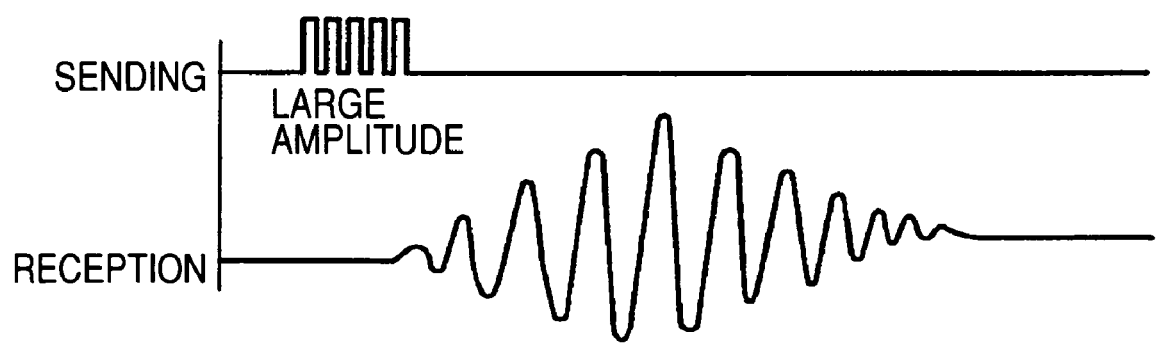

FIGS. 13A and 13B show that the signal intensity of the received ultrasonic signal in the ultrasonic receiver 3 changes in accordance with a change in the pulse amplitude of the ultrasonic signal output by the control circuit 4. FIGS. 13A and 13B show changes in the signal intensities of the received ultrasonic signals corresponding to the ultrasonic signals of different pulse amplitudes.

FIG. 13A is a diagram showing the change in the signal intensity of the received ultrasonic signal when the pulse amplitude of the ultrasonic signal is small.

FIG. 13B is a diagram showing the change in the signal intensity of the received ultrasonic signal when the pulse amplitude of the ultrasonic signal is large.

As shown in FIGS. 13A and 13B, in accordance with an increase in the pulse amplitude of the ultrasonic signal, the signal intensity of the received ultrasonic signal also increases. Consequently, the control circuit 4 controls so as to increase the pulse amplitude of the ultrasonic signal when the received ultrasonic signal is smaller than a prescribed value (S2), and so as to decrease the pulse amplitude of the ultrasonic signal when the received ultrasonic signal is greater than the prescribed value (S2). The control circuit 4 repeats the above-described operation of changing the pulse amplitude of the ultrasonic signal a plurality of times to thereby adjust the pulse amplitude so that the signal intensity of the received ultrasonic signal may become most approximate to the prescribed value (S2).

By the above-described control of the pulse amplitude of the ultrasonic signal by the control circuit 4, even when external factors affecting the reception of the ultrasonic change, the signal intensity of the received ultrasonic signal can be kept proper and therefore, the accuracy of double feed detection can be prevented from being reduced. That is, the double feed detecting apparatus 10 according to the present embodiment can control the pulse amplitude of the ultrasonic signal to thereby properly adjust the signal intensity of the received ultrasonic signal received by the ultrasonic receiver 3, and prevent a reduction in the accuracy of double feed detection caused by changes in the external factors.

As another embodiment, description will now be made of a method of adjusting the transmission efficiency of the received ultrasonic signal in the ultrasonic receiver 3 by the control circuit 4 changing the frequency of the ultrasonic signal.

Figure 14:
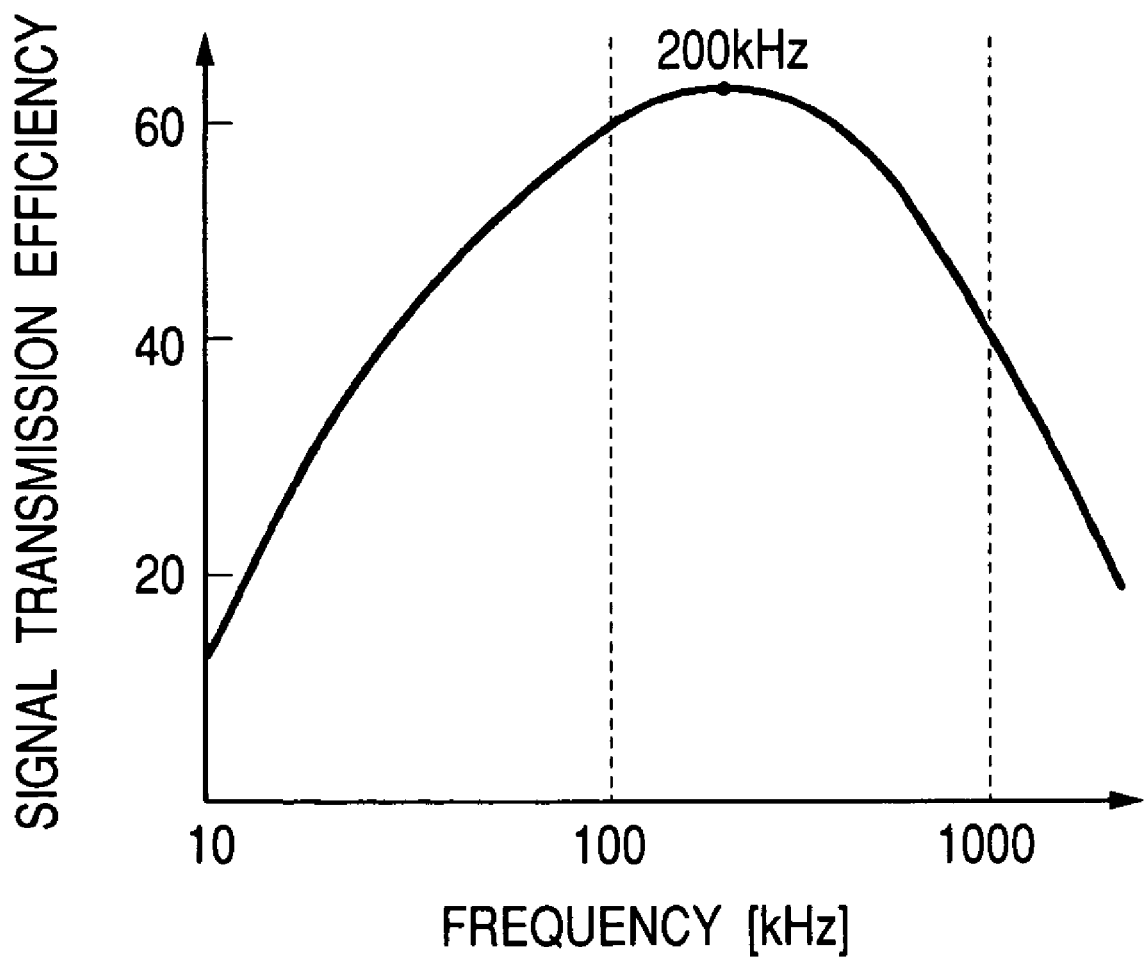
FIG. 14 shows the signal transmission efficiency-frequency characteristic of the received ultrasonic signal in the ultrasonic receiver 3.

FIG. 14 shows the signal transmission efficiency-frequency characteristic of the received ultrasonic signal in the ultrasonic receiver 3. In FIG. 14, the axis of ordinates represents the signal transmission efficiency [dB], and the axis of abscissas represents the frequency [kHz]. As shown in FIG. 14, the signal transmission efficiency is maximum in the vicinity of a frequency 200 kHz, and at frequencies equal to or less than 200 kHz and greater than 200 kHz, the signal transmission efficiency falls more for the values further from 200 kHz. The control circuit 4 in the present embodiment utilizes the characteristic shown in FIG. 14 to change the frequency of the ultrasonic signal, thereby adjusting the transmission efficiency of the received ultrasonic signal in the ultrasonic receiver 3. That is, the control circuit 4 can adjust the signal intensity of the received ultrasonic signal by the control of the frequency of the ultrasonic signal. In the present embodiment, the resonance frequency in the ultrasonic transmitter 2 and the ultrasonic receiver 3 is 200 kHz.

Figure 15A:
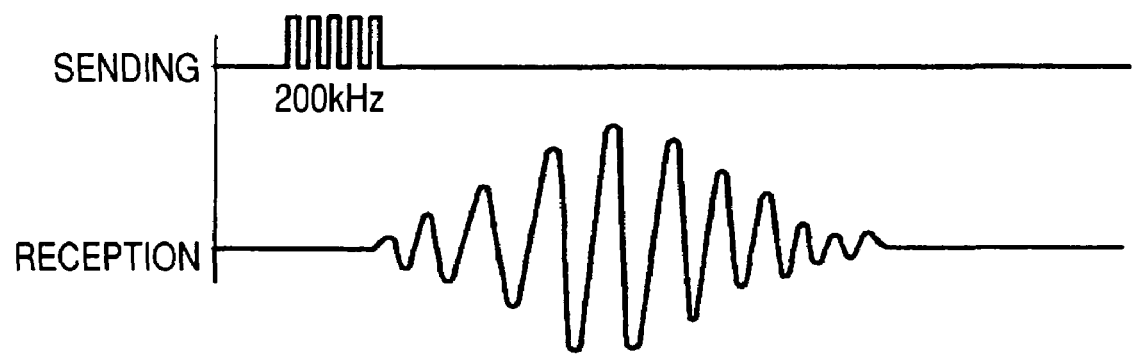
FIGS. 15A and 15B show changes in the signal intensity of the received ultrasonic signal at the frequencies of different ultrasonic signals.
Figure 15B:
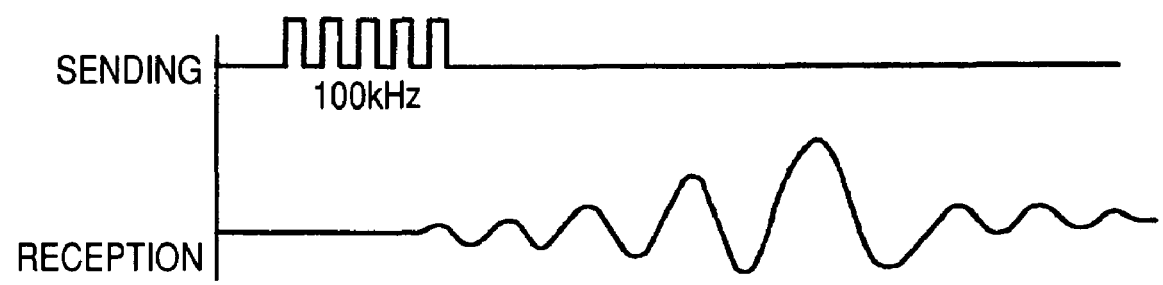

Reference is now had to FIGS. 15A and 15B to describe a change in the signal intensity of the received ultrasonic signal by a difference in the frequency of the ultrasonic signal. FIGS. 15A and 15B show changes in the signal intensity of the received ultrasonic signal at the different frequencies of the ultrasonic signal.

FIG. 15A shows a change in the signal intensity of the received ultrasonic signal when the frequency of the ultrasonic signal is 200 kHz.

FIG. 15B shows a change in the signal intensity of the received ultrasonic signal when the frequency of the ultrasonic signal is 100 kHz.

As shown in FIGS. 15A and 15B, as compared with the case of 200 kHz which is the resonance frequency in the ultrasonic transmitter 2 and the ultrasonic receiver 3, in the case of the frequency 100 kHz, the signal transmission efficiency decreases as shown in FIG. 14 and therefore, the signal intensity of the received ultrasonic signal also assumes a small value. Consequently, the control circuit 4 outputs an ultrasonic signal at a frequency more approximate to the above-described resonance frequency to thereby increase the signal intensity of the received ultrasonic signal, and outputs an ultrasonic signal at a frequency farther from the above-described resonance frequency, thereby effecting the control of decreasing the signal intensity of the received ultrasonic signal. By repeating the above-described operation of changing the frequency of the ultrasonic signal a plurality of times, the control circuit 4 adjusts the frequency of the ultrasonic signal so that the signal intensity of the received ultrasonic signal may become most approximate to the above-mentioned prescribed value (S2).

By the above-described control of the frequency of the ultrasonic signal in the control circuit 4, the signal intensity of the received ultrasonic signal can be kept proper even if the external factors affecting the reception of the ultrasonic change, and therefore the accuracy of double feed detection can be prevented from being reduced. That is, the double feed detecting apparatus 10 according to the present embodiment can control the frequency of the ultrasonic signal to thereby properly adjust the signal intensity of the received ultrasonic signal received by the ultrasonic receiver 3, and prevent a reduction in the accuracy of double feed detection caused by changes in the external factors As another embodiment, description will now be made of a method of adjusting the reception intensity of the received ultrasonic signal in the ultrasonic receiver 3 by the control circuit 4 changing the timing for obtaining the received ultrasonic signal.

Figure 16:
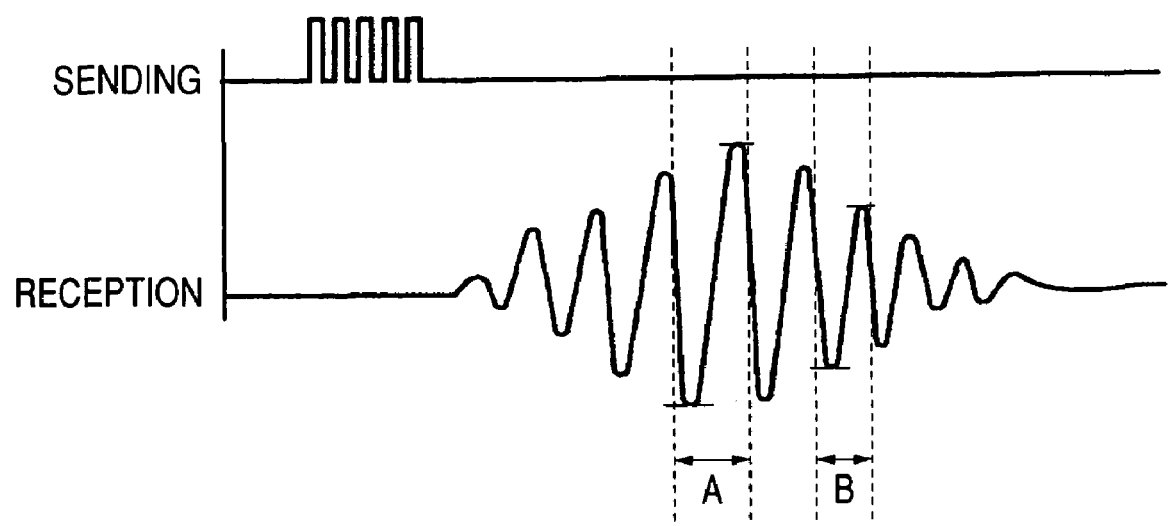
FIG. 16 shows a change in the reception intensity of the received ultrasonic signal by changing the timing for obtaining the received ultrasonic signal.

FIG. 16 shows a change in the reception intensity of the received ultrasonic signal caused by changing the timing for obtaining the received ultrasonic signal. In FIG. 16, a range A indicates a range corresponding to a period during which the reception intensity becomes maximum, and a range B indicates a range corresponding to a period during which the reception intensity is not maximum (the third or fourth greatest). That is, the range A indicates an obtainment range at the timing whereat the reception intensity of the received ultrasonic signal becomes maximum. Also, the range B indicates an obtainment range at the timing whereat the reception intensity of the received ultrasonic signal becomes the third or fourth greatest.

A method of calculating the above-described timing will now be described. For example, the ultrasonic reaching time t=D/340 [s] is calculated from the distance d [m] from the ultrasonic transmitter 2 to the ultrasonic receiver 3 and the propagation speed 340 [m/s] of the ultrasonic. Thereby, when the received ultrasonic signal is obtained in t [s] after the pulse of the ultrasonic transmitted lastly by the ultrasonic transmitter 2, the vicinity of the maximum value (range A) of the reception intensity can be obtained. Also, the ultrasonic obtainment time can be obtained while being deviated from the vicinity of the maximum value of the signal intensity to thereby obtain the range B. As is apparent also from FIG. 16, the reception intensity of the received ultrasonic signal is more decreased in the range B than in the range A.

By the utilization of the above-described characteristic of the received ultrasonic signal, the control circuit 4 effects the control of obtaining the received ultrasonic signal at timing nearer to the timing at which the reception intensity becomes maximum (the timing of the range A) to thereby increase the reception intensity of the received ultrasonic signal, and obtaining the received ultrasonic signal at timing farther from the timing at which the reception intensity becomes maximum to thereby decrease the reception intensity of the received ultrasonic signal. The control circuit 4 repeats the above-described changing operation a plurality of times to thereby adjust the obtaining timing of the received ultrasonic signal (hereinafter referred to as the ultrasonic obtaining timing) so that the signal intensity of the received ultrasonic signal may become most approximate to the prescribed value (S2).

That is, the ultrasonic obtaining timing after the ultrasonic has been transmitted is approximated to the ultrasonic reaching time from the ultrasonic transmitter 2 to the ultrasonic receiver 3, whereby the reception intensity of the received ultrasonic signal is increased, and the ultrasonic obtaining timing is made farther from the ultrasonic reaching time, whereby the reception intensity of the received ultrasonic signal is decreased. The control circuit 4 repeats the above-described changing operation for the obtaining timing of the received ultrasonic signal a plurality of times to thereby adjust the ultrasonic obtaining timing so that the reception intensity (signal intensity) of the received ultrasonic signal may become most approximate to the prescribed value (S2).

By the above-described control of the ultrasonic obtaining timing in the control circuit 4, even when the external factors which affect the reception of the ultrasonic have changed, the reception intensity of the received ultrasonic signal can be kept proper and therefore, the accuracy of double feed detection can be prevented from being reduced. That is, the double feed detecting apparatus 10 according to the present embodiment can control the ultrasonic obtaining timing to thereby properly adjust the reception intensity of the received ultrasonic signal received by the ultrasonic receiver 3, and prevent any reduction in the accuracy of double feed detection caused by changes in the external factors.

As another embodiment, description will now be made of a method of adjusting the reception intensity of the received ultrasonic signal in the ultrasonic receiver 3 by the control circuit 4 utilizing the above-described four functions.

For example, when the paper 1 is not inserted between the ultrasonic transmitter 2 and the ultrasonic receiver 3, the control circuit 4 executes the adjustment of the reception intensity by the following control. The control circuit 4 optimizes each of the pulse number of the ultrasonic signal, the pulse amplitude of the ultrasonic signal, the frequency of the ultrasonic signal and the ultrasonic obtaining timing described above to thereby adjust the signal intensity of the received ultrasonic signal.

A specific method of adjusting the signal intensity of the received ultrasonic signal will be described hereinafter. A signal analyzing circuit 8 is provided between the control circuit 4 and the A-D converter 7 shown in FIG. 1, and when the paper 1 is not inserted between the ultrasonic transmitter 2 and the ultrasonic receiver 3, the signal analyzing circuit 8 compares the signal intensity of the received ultrasonic signal having directly received a propagated ultrasonic with the preset prescribed value (S2).

Next, on the basis of the result of the comparison, the control circuit 4 utilizes each function as required to optimize and determine the pulse number, pulse amplitude and frequency of the ultrasonic signal and the ultrasonic obtaining timing. Also, a storage device 9 connected to the control circuit 4 hold therein the pulse number, pulse amplitude and frequency of the ultrasonic signal and the ultrasonic obtaining timing determined by the control circuit 4 as set values.

As described above, the control circuit 4 can use a plurality of functions of adjusting the signal intensity by one or more combinations to thereby more flexibly cope with changes in the external factors and maintain the accuracy of double feed detection.

For example, when the adjustment of the signal intensity is to be effected with a plurality of functions combined together, the adjustment of the signal intensity of the received ultrasonic signal by the control of the pulse number of the ultrasonic signal cannot be done finely and therefore, the control circuit 4 is utilized only when a power source is switched on. Also, when the signal intensity of the received ultrasonic signal is to be adjusted each time the paper 1 is transported, the control circuit 4 utilizes one or a combination of more of the function of controlling the pulse amplitude of the ultrasonic signal, the function of controlling the frequency of the ultrasonic signal and the function of controlling the ultrasonic obtaining timing to adjust the signal intensity of the received ultrasonic signal.

Also, when after the adjustment of the signal intensity, the paper 1 has been inserted between the ultrasonic transmitter 2 and the ultrasonic receiver 3, the control circuit 4 performs double feed detection by the above-described adjustment by the use of the set values of the pulse amplitude and frequency of the ultrasonic signal and the ultrasonic obtaining timing held in the storage device 9. During the time when the paper 1 is inserted between the ultrasonic transmitter 2 and the ultrasonic receiver 3, the received ultrasonic signal fluctuates and therefore, the above-described adjustment of the signal intensity is not effected. Also, the control circuit 4 may adjust the signal intensity after a sheet material for setting the prescribed value (S2) has been inserted between the ultrasonic transmitter 2 and the ultrasonic receiver 3.

As another embodiments, description will now be made of a construction in which the double feed detecting apparatus 10 is incorporated, for example, in an apparatus such as a scanner, a printer, a copying machine, a printing machine or an ATM and detects the double feed of the paper 1.

FIG. 17 is a flow chart showing the operation of the double feed detecting apparatus 10. As shown in FIG. 17, first at a step S1801, the power source of the apparatus provided with the double feed detecting apparatus 10 is switched on, whereby the apparatus and the double feed detecting apparatus 10 are activated. Next, at a step S1802, the double feed detecting apparatus 10 confirms whether the paper 1 is inserted between the ultrasonic transmitter 2 and the ultrasonic receiver 3. If the paper 1 is inserted (YES at the step S1802), advance is made to a step S1803, where the signal analyzing circuit 8 carries out the process of detecting the double feed of the paper 1. When the process of this step S1803 is finished, the double feed detecting apparatus 10 again confirms whether the paper 1 is inserted between the ultrasonic transmitter 2 and the ultrasonic receiver 3.

Also, if the paper 1 is not inserted (NO at the step S1802), advance is made to a step S1804, where the control circuit 4 adjusts the signal intensity of the received ultrasonic signal. Next, at a step S1805, the storage device 9 holds a set value obtained in the process of the step S1804. When the process of this step S1805 is finished, return is made to the step S1802, where the double feed detecting apparatus 10 again confirms whether the paper 1 is inserted between the ultrasonic transmitter 2 and the ultrasonic receiver 3.

As described above, during the time when the paper 1 is not transported, the double feed detecting apparatus 10 according to the present embodiment performs the adjustment of the signal intensity of the received ultrasonic signal, whereby even when the external factors to the double feed detecting apparatus 10 in the apparatus change, the double feed detecting apparatus 10 can keep the signal intensity of the received ultrasonic signal proper and therefore, can prevent the accuracy of double feed detection from being reduced.

As another embodiment, description will now be made of a method whereby the control circuit 4 controls the time interval of the transmission of the ultrasonic signal in accordance with a change in the convergence time of the ultrasonic.

Figure 18A:
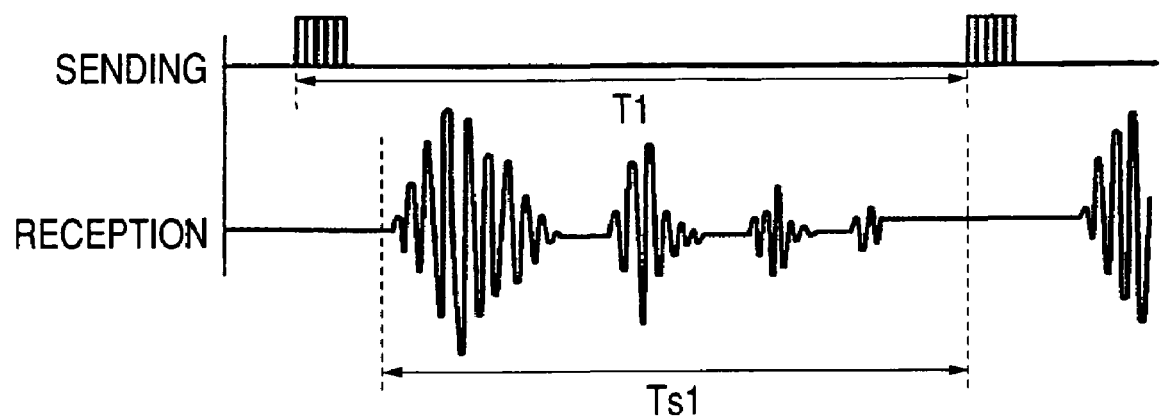
FIGS. 18A and 18B show a change in the convergence time of the received ultrasonic signal by the presence or absence of an interceptor and the time interval of the transmission of the ultrasonic signal conforming to the convergence time.
Figure 18B:
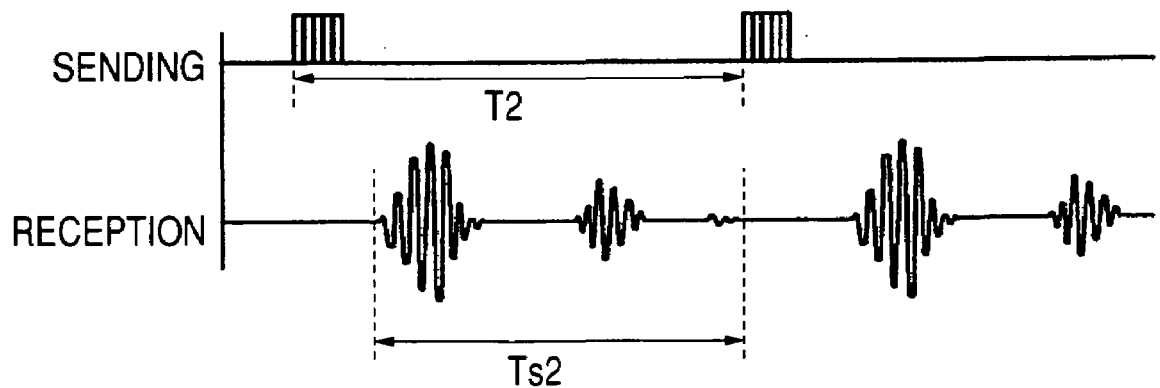

FIGS. 18A and 18B show a change in the convergence time of the received ultrasonic signal by the presence or absence of an interceptor and the time interval of the transmission of the ultrasonic signal conforming to the convergence time.

FIG. 18A indicates the time interval T1 of the sending of the ultrasonic signal and the convergence time Ts1 of the received ultrasonic signal when the paper 1 which is an interceptor is not inserted between the ultrasonic transmitter 2 and the ultrasonic receiver 3.

FIG. 18B indicates the time interval T2 of the transmission of the ultrasonic signal and the convergence time Ts2 of the received ultrasonic signal when the paper 1 which is an interceptor is inserted between the ultrasonic transmitter 2 and the ultrasonic receiver 3.

As shown in FIGS. 18A and 18B, the convergence time Ts1 of the received ultrasonic signal when the paper 1 is not inserted is longer in the time required for convergence than the convergence time Ts2 of the received ultrasonic signal when the paper 1 is inserted. That is, the paper 1 becomes an interceptor, whereby the ultrasonic is quickly converged, whereby the received ultrasonic signal is also quickly converged when the paper 1 is inserted. In conformity therewith, the time interval T2 of the sending of the ultrasonic signal also becomes shorter than the time interval T1 of the transmission of the ultrasonic signal.

Here, description will be made of the relation between the time interval of the sending of the ultrasonic signal and the convergence time of the received ultrasonic signal. If the burst-wave of the ultrasonic signal is transmitted while the reverberation of the ultrasonic repeating reflection while being attenuated sufficiently remains in the transport path for the paper 1 (sheet material), interference is caused and the waveform of the ultrasonic signal is changed and therefore, the accuracy of double feed detection is reduced. In order to avoid the interference between this newly transmitted ultrasonic and the reverberation of the ultrasonic transmitted at the last time, it is necessary to provide a constant time interval in the burst-wave of the ultrasonic signal. To set this time interval, it is necessary to detect the attenuation of the reverberation of the ultrasonic. In the present embodiment, the signal analyzing circuit 8 detects the convergence of the received ultrasonic signal to thereby detect the attenuation of the reverberation of the ultrasonic.

As described above, between a case where the interceptor is present between the ultrasonic transmitter 2 and the ultrasonic receiver 3 and a case where the ultrasonic directly reaches the ultrasonic receiver 3, or depending on the material of the interceptor inserted between the ultrasonic transmitter 2 and the ultrasonic receiver 3, there is a time difference in the convergence of the ultrasonic in the transport path for the sheet material. Particularly, when the interceptor is present, the ultrasonic is rapidly converged and therefore, if the ultrasonic signal is transmitted at the same time interval as the time interval T1 of the transmission of the ultrasonic signal when the interceptor is not present, there is the problem of an excessive waiting time. The control circuit 4 in the present embodiment controls the ultrasonic signal so as to effect the transmission at the time interval T2 in order to solve the above-noted problem and effect the efficient transmission of the ultrasonic signal.

Specifically, the signal analyzing circuit 8 monitors the maximum amplitude of the received ultrasonic signal each time the paper 1 is transported, and calculates the convergence time (Ts1 or Ts2 in FIG. 18A or 18B) until converged from the maximum amplitude. The control circuit 4 determines the appropriate time interval of the burst transmission of the ultrasonic on the basis of the convergence time calculated by the signal analyzing circuit 8. Thus, the double feed detecting apparatus 10 according to the present embodiment performs the burst transmission of the ultrasonic at an appropriate time interval, whereby it can increase the number of times of sampling while preventing the interference between the ultrasonic and the reverberation thereof. Thereby, the information amount of the received ultrasonic signal per unit time is increased and the accuracy of double feed detection is improved.

The method whereby the signal analyzing circuit 8 calculates the convergence time is not restricted to the above-described method, but may be, for example, a method whereby the signal analyzing circuit 8 obtains the amplitude of the received ultrasonic signal having received the reverberation of the ultrasonic repeating reflection while being attenuated on the transport path for the sheet material (hereinafter simply referred to as the amplitude of the reverberation), and determines whether the amplitude of the reverberation is smaller than a prescribed value (S3) to thereby determine the convergence of the ultrasonic, and calculate as the convergence time the time from after the reception of the ultrasonic is started until the convergence is determined. Also, while in the above-described embodiment, the control circuit determines the time interval of the transmission of the ultrasonic signal from the convergence time, there is not restrictive, but the signal analyzing circuit 8 may calculate the time interval of the transmission of the ultrasonic signal together with the convergence time. Also, when the signal analyzing circuit 8 monitors the maximum amplitude of the received ultrasonic signal each time the paper 1 is transferred; it may calculate the time interval of the transmission of the ultrasonic signal from the maximum amplitude.

Description will now be made of the operation of determining the time interval of the transmission of the ultrasonic signal in the double feed detecting apparatus 10. It is to be understood that the double feed detecting apparatus 10 according to the present embodiment is incorporated in an apparatus such as a scanner, a printer, a copying machine, a printing machine or an ATM, and is designed to detect the double feed of the paper 1.

Figure 19:
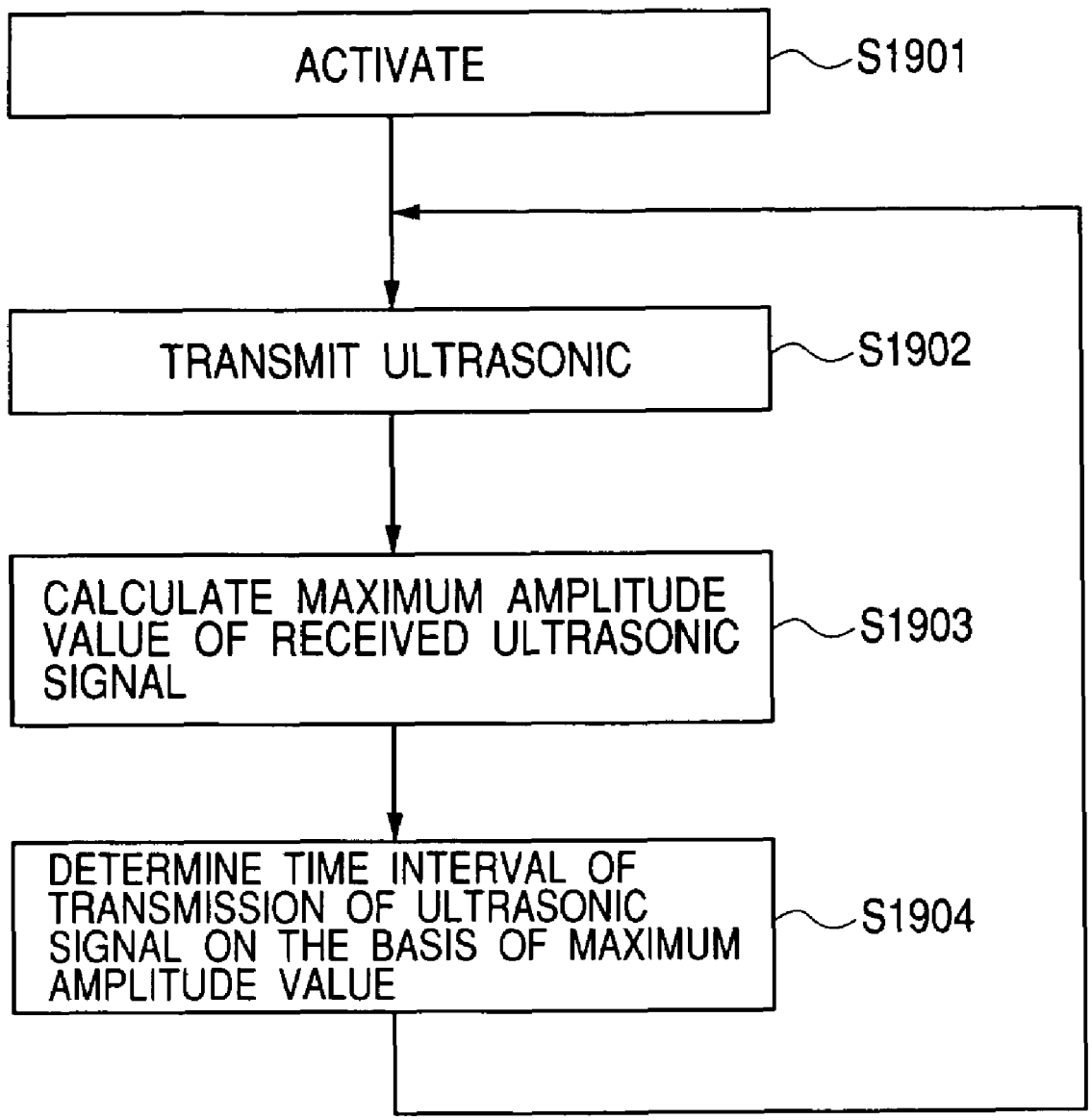
FIG. 19 is a flow chart showing the operation of determining the time interval of the transmission of the ultrasonic signal in the double feed detecting apparatus 10.
Figure 20:
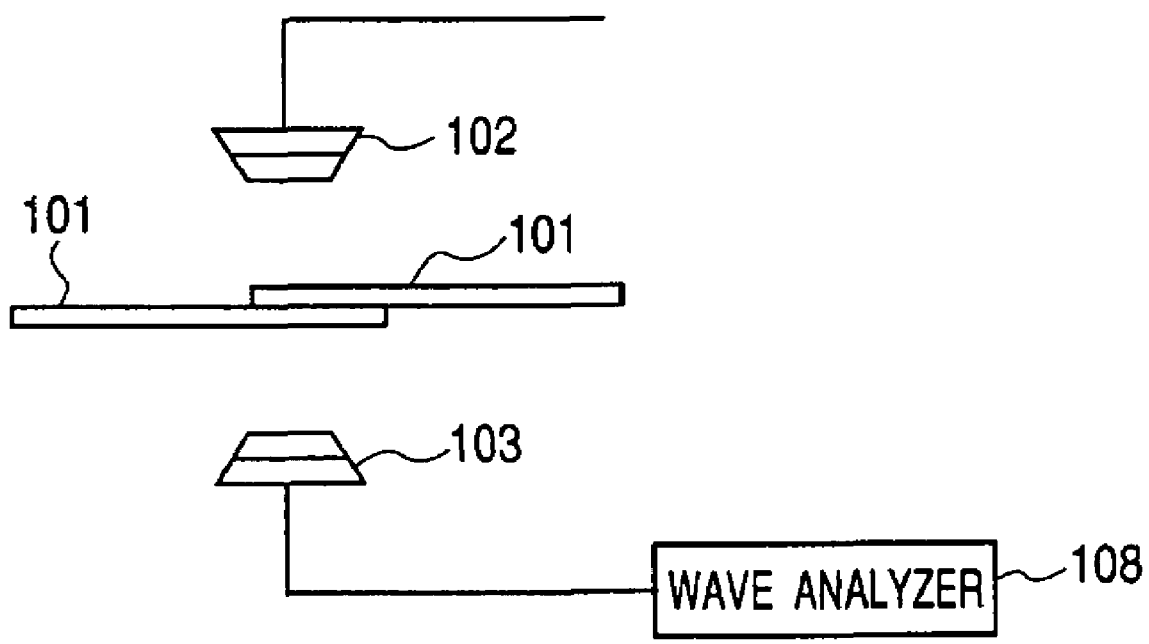
FIG. 20 shows the epitome of a conventional double feed detecting apparatus.
Figure 21:
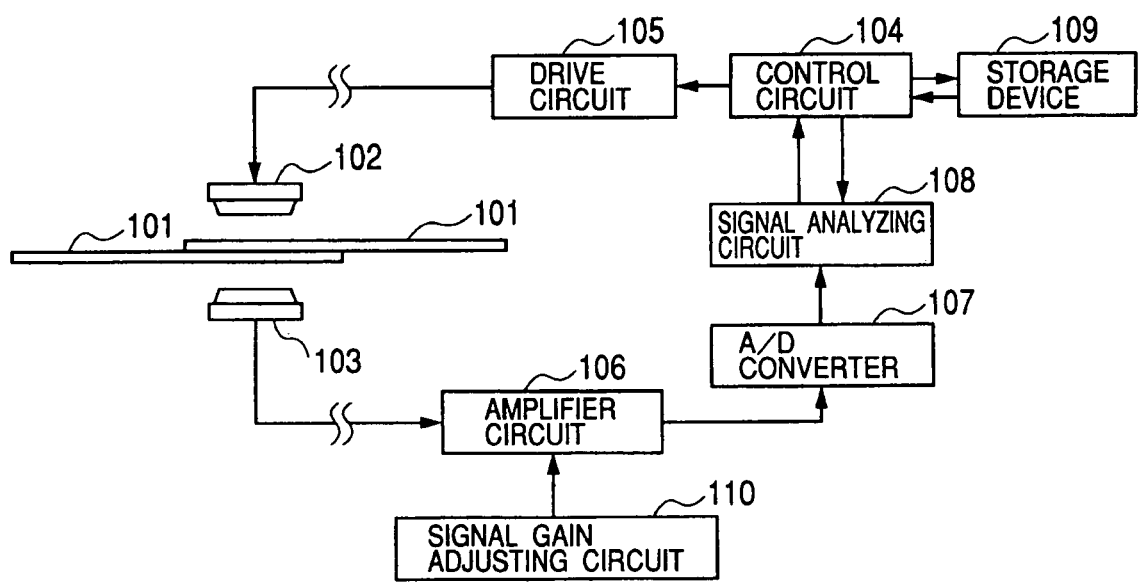
FIG. 21 shows the epitome of a conventional double feed detecting apparatus.

FIG. 19 is a flow chart showing the operation of determining the time interval of the transmission of the ultrasonic signal in the double feed detecting apparatus 10.

As shown in FIG. 19, when at a step S1901, the power source of the apparatus is switched on, the apparatus and the double feed detecting apparatus 10 are activated. Next, at a step S1902, the ultrasonic transmitter 2 transmits an ultrasonic. Thereby, the ultrasonic receiver 3 receives the ultrasonic and outputs a received ultrasonic signal, and the A-D, converter 7 digitizes the received ultrasonic signal. Next, at a step S1903, the signal analyzing circuit 8 analyzes the digitized received ultrasonic signal and calculates the value of the maximum amplitude thereof. Next, at a step S1904, the signal analyzing circuit 8 and the control circuit 4 calculate the convergence time of the received ultrasonic signal on the basis of the value of the maximum amplitude of the received ultrasonic signal, and determine the time interval of the transmission of the ultrasonic signal on the basis of the convergence time. Thereby, the control circuit 4 outputs an ultrasonic signal at the determined time interval, and the drive circuit 5 having received it amplifies the ultrasonic signal and outputs an ultrasonic pulse signal, and the ultrasonic transmitter 2 having received it transmits an ultrasonic conforming to the ultrasonic pulse signal (return is made to the step S1902). That is, the ultrasonic transmitter 2 transmits the burst signal of the ultrasonic at the time interval determined by the control circuit 4.

Also, the process carried out by the control circuit 4 and the signal analyzing circuit 8 shown in FIGS. 17 and 19 may be ones realized by hardware for exclusive use constituting the control circuit 4 and the signal analyzing circuit 8, and the control circuit 4 or the signal analyzing circuit 8 may be comprised of a memory and a central processing unit (CPU), and read a program for realizing a function undertaking each process into the memory and execute the program to thereby realize the function.

Also, it is to be understood that the above-mentioned memory is comprised of a nonvolatile memory such as a hard disc device, a magneto-optical disc device or a flash memory, a recording medium such as a CD-ROM capable of reading only, a volatile memory like a random access memory (RAM), or computer-readable and computer-writable recording medium comprising a combination of these.

Also, the "computer-readable recording medium" refers to a portable medium such as a flexible disc, a magneto-optical disc, a ROM or a CD-ROM, or a storage device such as a hard disc contained in a computer system. Further, it is to be understood that the "computer-readable recording medium" includes one holding a program therein for a predetermined time, like a volatile memory (RAM) in the CPU in the control circuit which is a server or a client when the program is sent through a network such as the Internet or a communication circuit such as a telephone circuit.

Also, the above-mentioned program may be transmitted from a computer system storing this program in a memory or the like to a memory in the control circuit through a transmitting medium or by a transmitting wave in the transmitting medium. Here, the "transmitting medium" which transmits the program therethrough refers to a medium having the function of transmitting information, like a network (communications net) such as the Internet or a communication circuit (communication line) such as a telephone circuit.

Also, the above-mentioned program may be one for realizing part of the aforedescribed function. Further, it may be what can be realized by a combination with a program having the aforedescribed function already recorded in the memory in the control circuit 4, i.e., a so-called differential file (differential program).

Also, a program product such as a computer-readable recording medium having the above-mentioned program recorded therein can be applied as an embodiment of the present invention.

While the embodiments of the present invention have been described in detail above, specific constructions are not restricted to these embodiments, but cover designs or the like within a scope which does not depart from the gist of this invention.

What is claimed is:

1. A double feed detecting apparatus comprising:
ultrasonic transmitting means installed on one side of a transport path for a sheet material for transmitting an ultrasonic wave toward the sheet material;
ultrasonic receiving means installed on the other side of the transport path for the sheet material for receiving the ultrasonic wave transmitted by said ultrasonic transmitting means and outputting a received ultrasonic signal;
first double feed determining means for determining whether double feed is arising or not in accordance with an amplitude of the received ultrasonic signal output by said ultrasonic receiving means; and
second double feed determining means for determining whether double feed is arising or not in accordance with a phase of the received ultrasonic signal output by said ultrasonic receiving means,
wherein said first double feed determining means calculates an amplitude of a noise signal received by said ultrasonic receiving means while said ultrasonic transmitting means does not transmit the ultrasonic wave, and determines whether a double feed is occurring or not on the basis of a change in the amplitude of the received ultrasonic signal and a change in the calculated amplitude of the noise signal.

2. A double feed detecting apparatus according to claim 1, further comprising sampling means for foreseeing sampling timing at which the amplitude of the received ultrasonic signal becomes maximum, from a distance from said ultrasonic transmitting means to said ultrasonic receiving means, and a propagation speed of the ultrasonic wave, and for sampling the received ultrasonic signal at the foreseen sampling timing a plurality of times to obtain a plurality of the sampled ultrasonic signals, wherein said first double feed determining means and said second double feed determining means process the sampled ultrasonic signals to detect the amplitude and the phase of the received ultrasonic signal.

3. A double feed detecting apparatus according to claim 2, wherein said sampling means averages data corresponding to the plurality of times of sampling of the received ultrasonic signal by sampling point.

4. A double feed detecting apparatus according to claim 1, wherein said first double feed determining means calculates the amplitude of the noise signal immediately before said ultrasonic transmitting means transmits the ultrasonic wave.

5. A double feed detecting apparatus comprising:
ultrasonic transmitting means installed on one side of a transport path for a sheet material for transmitting an ultrasonic wave toward the sheet material;
ultrasonic receiving means installed on the other side of the transport path for the sheet material for receiving the ultrasonic wave transmitted by said ultrasonic transmitting means and outputting a received ultrasonic signal;
first double feed determining means for determining whether double feed is arising or not in accordance with an amplitude of the received ultrasonic signal output by said ultrasonic receiving means;
second double feed determining means for determining whether double feed is arising or not in accordance with a phase of the received ultrasonic signal output by said ultrasonic receiving means;
phase information obtaining means for obtaining information of a phase of the received ultrasonic signal in a state in which the amplitude of the received ultrasonic signal output by said ultrasonic receiving means becomes maximum; and
basic phase information holding means for holding and storing therein basic phase information of the received ultrasonic signal obtained by said phase information obtaining means when said ultrasonic receiving means has directly received the ultrasonic wave transmitted by said ultrasonic transmitting means,
wherein said second double feed determining means compares the phase information of the received ultrasonic signal obtained by said phase information obtaining means when said ultrasonic receiving means has received the ultrasonic wave transmitted from said ultrasonic transmitting means. through the sheet material, with the basic phase information held by said basic phase information holding means to thereby determine whether double feed is arising or not.

6. A double feed detecting apparatus according to claim 5, wherein said basic phase information holding means renews the basic phase information every time the sheet material is transported.

7. A double feed detecting apparatus according to claim 6, further comprising:
signal amplifying means for amplifying the received ultrasonic signal output by said ultrasonic receiving means at plural kinds of amplification factors; and
information holding timing forming means for forming a timing signal for controlling timing, at which said phase information obtaining means obtains the information of the basic phase, on the basis of a change in the amplitude of the received ultrasonic signal which has been amplified at first amplification factor by said signal amplifying means within a range in which the received ultrasonic signal has not been saturated,
wherein said phase information obtaining means obtains the basic phase information from the received ultrasonic signal which has been amplified at second amplification factor and has been saturated by said signal amplifying means, in correspondence with the timing signal, and said second double feed determining means compares the basic phase information and a phase of the received ultrasonic signal amplified at the second amplification factor to thereby effect the determination of double feed.

8. A double feed detecting apparatus according to claim 7, wherein said signal amplifying means amplifies the received ultrasonic signal at plural kinds of amplification factors by a construction in which a plurality of signal amplifying circuits are series-connected and each connection point is output.

9. A double feed detecting apparatus according to claim 7, wherein said signal amplifying means amplifies the received ultrasonic signal at plural kinds of amplification factors by a construction in which signal amplifying circuits of plural kinds of amplification factors are parallel-connected and output is effected from each of the signal amplifying circuits.

10. A double feed detecting apparatus comprising:
ultrasonic transmitting means installed on one side of a transport path for a sheet material for transmitting an ultrasonic wave toward the sheet material;
ultrasonic receiving means installed on the other side of the transport path for the sheet material for receiving said ultrasonic wave and outputting a received ultrasonic signal;
control means for adjusting an amplitude of the received ultrasonic signal of said ultrasonic receiving means to a prescribed value, by altering at least one of an obtaining timing of the received ultrasonic signal or a characteristic of the ultrasonic wave transmitted by said ultrasonic transmitting means; and
signal analyzing means for analyzing whether a double feed is occurring or not on the basis of a change in the amplitude of the received ultrasonic signal output by said ultrasonic receiving means which has been adjusted by said control means.

11. A double feed detecting apparatus according to claim 10, wherein the ultrasonic wave transmitted by said ultrasonic transmitting means is an ultrasonic burst-wave, and the characteristic of the ultrasonic wave transmitted by said ultrasonic transmitting means which is controlled by said control means is a pulse number in the ultrasonic burst-wave.

12. A double feed detecting apparatus according to claim 10, wherein the characteristic of the ultrasonic wave transmitted by said ultrasonic transmitting means which is controlled by said control means is a pulse amplitude of the ultrasonic wave.

13. A double feed detecting apparatus according to claim 10, wherein the characteristic of the ultrasonic wave transmitted by said ultrasonic transmitting means which is controlled by said control means is a frequency of the ultrasonic wave.

14. A double feed detecting apparatus according to claim 10, wherein the ultrasonic wave transmitted by said ultrasonic transmitting means is an ultrasonic burst-wave, and the obtaining timing of the received ultrasonic signal controlled by said control means is timing for obtaining the received ultrasonic signal assuming a desired amplitude by the utilization of the fact that the amplitude of the received ultrasonic signal generated by the ultrasonic burst-wave is increased or decreased by the lapse of time.

15. A double feed detecting apparatus according to claim 10, wherein the ultrasonic wave transmitted by said ultrasonic transmitting means is an ultrasonic burst-wave, and the characteristic of the ultrasonic wave transmitted by said ultrasonic transmitting means which is controlled by said control means is one or a combination of a pulse number, a pulse amplitude and a frequency in the ultrasonic burst-wave, and the obtaining timing of the received ultrasonic signal controlled by said control means is a timing for obtaining the received ultrasonic signal assuming a desired amplitude by the utilization of the fact that the amplitude of the received ultrasonic signal generated by the ultrasonic burst-wave is increased or decreased by the lapse of time.

16. A double feed detecting apparatus according to claim 10, wherein when a plurality of the sheet materials are being continuously transported at a predetermined interval, said control means performs control for adjusting the amplitude of the received ultrasonic signal before each sheet material passes between said ultrasonic transmitting means and said ultrasonic receiving means.

17. A double feed detecting apparatus comprising:
ultrasonic transmitting means installed on one side of a transport path for a sheet material for transmitting an ultrasonic burst-wave toward the sheet material at an arbitrary time interval;
ultrasonic receiving means installed on the other side of the transport path for the sheet material for receiving the ultrasonic burst-wave transmitted by said ultrasonic transmitting means and outputting a received ultrasonic signal;
signal analyzing means for analyzing convergence time that is required for convergence of the received ultrasonic signal output by said ultrasonic receiving means, analyzing a change in the convergence time, and analyzing whether a double feed is occurring or not on the basis of a change in an amplitude of the received ultrasonic signal output by said ultrasonic receiving means; and
control means for controlling said ultrasonic transmitting means so as to change the time interval at which the ultrasonic burst-wave is transmitted, in accordance with the change in the convergence time analyzed by said signal analyzing means.

18. A double feed detecting apparatus according to claim 17, wherein said signal analyzing means obtains a maximum amplitude value while monitoring amplitude of the received ultrasonic signal, and calculates the convergence time on the basis of the obtained maximum amplitude value.

19. A double feed detecting apparatus according to claim 17, wherein said signal analyzing means utilizes a threshold value of an amplitude for judging the convergence of the received ultrasonic signal to calculate the convergence time by calculating a time from the start of reception of the received ultrasonic signal until the moment at which the amplitude of the received ultrasonic signal becomes equal to or less than the threshold value.

* * * * *